United States Patent [19]

Coates et al.

[11] Patent Number: 4,636,521
[45] Date of Patent: Jan. 13, 1987

[54] 3 AMINO ALKYL INDOLES FOR USE IN TREATING MIGRAINE

[75] Inventors: Ian H. Coates, Hertford; Keith Mills, Ware; Colin F. Webb, Royston; Michael D. Dowle; David E. Bays, both of Ware, all of United Kingdom

[73] Assignee: Glaxo Group Limited, London, England

[21] Appl. No.: 626,383

[22] Filed: Jun. 29, 1984

Related U.S. Application Data

[63] Continuation of Ser. No. 404,872, Aug. 3, 1982, which is a continuation of Ser. No. 292,022, Aug. 11, 1981.

[30] Foreign Application Priority Data

Aug. 12, 1980 [GB] United Kingdom ................ 8026288

[51] Int. Cl.$^4$ .................... A61K 31/40; C07D 209/14
[52] U.S. Cl. .................................. 514/415; 514/212; 514/323; 514/414; 546/201; 548/504; 548/507; 540/602
[58] Field of Search ...................... 548/503, 504, 507; 260/239 B, 245.7; 546/201; 514/323, 212, 415, 414

[56] References Cited

U.S. PATENT DOCUMENTS 3,472,870 10/1969 Larsen et al. ...................... 548/504
4,064,255 12/1977 Champseix et al. ................ 424/267
4,180,509 12/1979 Metcalf et al. ...................... 548/495
4,252,803  2/1981 Webb ............................... 424/248.5

FOREIGN PATENT DOCUMENTS 632051 11/1963 Belgium ........................... 548/503

OTHER PUBLICATIONS

Espamer V., "Gramine Derivatives Antagonistic to 5-Hydroxytryptamine," *Science* 121: 369–370 (1955).
Freter et al., "Amidomethylierung Indolen," *Liebigs Ann. Chem.* 1976, pp. 241–249.
Shaw., New Agents Inhibitory to ... Effects of Serotonin," *Chem. Abst.* 50:14127 (1955).
Shaw and Woolley, "Indole Carboxamidines and Aminomethylindoles . . . ," *J.A.C.S.* vol. 79: pp. 3561–3564 (1957).

*Primary Examiner*—Glenna M. Hendricks
*Attorney, Agent, or Firm*—Bacon & Thomas

[57] ABSTRACT

Compounds are disclosed of general formula (I)

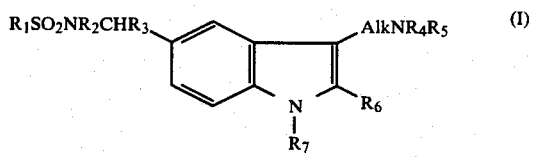

wherein
$R_1$ represents an alkyl, cycloalkyl, aryl or aralkyl group;
$R_2$, $R_3$, $R_4$, $R_6$ and $R_7$, which may be the same or different, each represents a hydrogen atom or a $C_{1-3}$ alkyl group;
$R_5$ represents a hydrogen atom or an alkyl, cycloalkyl, alkenyl or an aralkyl group; or $R_4$ and $R_5$ together form an aralkylidene group or $R_4$ and $R_5$ together with the nitrogen atom to which they are attached form a saturated monocyclic 5- to 7-membered ring; Alk represents an alkylene chain containing two or three carbon atoms which may be unsubstituted or substituted by not more than two $C_{1-3}$ alkyl groups; and physiologically acceptable salts, solvates and bioprecursors thereof. The compounds are described as potentially useful for the treatment of migraine and may be formulated as pharmaceutical compositions in conventional manner using one or more pharmaceutically acceptable carriers or excipients. Various processes for the preparation of the compounds are disclosed including, for example, a process involving reaction of an aminoalkyl indole with a sulphonylating agent in order to introduce the —SO$_2$— group at the 5-position on the indole nucleus.

13 Claims, No Drawings

3 AMINO ALKYL INDOLES FOR USE IN TREATING MIGRAINE

This application is a continuation of application Ser. No. 404,872, filed Aug. 3, 1982, which is a continuation of Ser. No. 292,022, filed Aug. 11, 1981.

This invention relates to heterocyclic compounds, to processes for their preparation, to pharmaceutical compositions containing them and to their medical use.

The present invention provides an indole of the general formula (I):

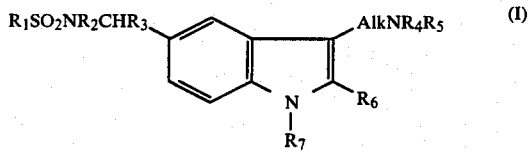

wherein
$R_1$ represents an alkyl, cycloalkyl, aryl or aralkyl group;
$R_2$, $R_3$, $R_4$, $R_6$ and $R_7$, which may be the same or different, each represents a hydrogen atom or a $C_{1-3}$ alkyl group;
$R_5$ represents a hydrogen atom or an alkyl, cycloalkyl, alkenyl or aralkyl group; or $R_4$ and $R_5$ together form an aralkylidene group or $R_4$ and $R_5$ together with the nitrogen atom to which they are attached form a saturated monocyclic 5- to 7-membered ring; Alk represents an alkylene chain containing two or three carbon atoms which may be unsubstituted or substituted by not more than two $C_{1-3}$ alkyl groups;
and physiologically acceptable salts, solvates (e.g. hydrates) and bioprecursors thereof.

The compounds according to the invention include all optical isomers thereof and their racemic mixtures.

Referring to the general formula (I) the alkyl groups may be straight chain or branched chain alkyl groups and they preferably contain from 1 to 6 carbon atoms unless otherwise specified. The alkyl group represented by $R_1$ may be unsubstituted or substituted by one to three halogen atoms e.g. fluorine. The cycloalkyl groups preferably contain 5 to 7 carbon atoms. The term aryl, used as such or in the term aralkyl, preferably means phenyl which may be unsubstituted or substituted by one or more ($C_{1-3}$) alkyl groups e.g. methyl, halogen atoms e.g. fluorine, or hydroxy or ($C_{1-3}$) alkoxy groups e.g. methoxy. The alkyl moiety of the aralkyl groups preferably contains 1 to 4 carbon atoms. The aralkylidene group is preferably an arylmethylidene group. The alkenyl groups preferably contain 3 to 6 carbon atoms.

Suitable physiologically acceptable salts of the indoles of general formula (I) include acid addition salts formed with organic or inorganic acids for example hydrochlorides, hydrobromides, sulphates, fumarates, and maleates. Other salts may be useful in the preparation of compounds of formula (I), e.g. creatinine sulphate adducts.

The term "bioprecursors" used herein means compounds which have a structure different from that of the compounds of formula (I) but which, upon administration to an animal or human being, are converted in the body to a compound of formula (I).

The compounds of the invention mimic methysergide in contacting the dog isolated saphenous vein strip (E. Apperley et al., Br. J. Pharmacol., 1980, 68, 215-224) and, like methysergide, they have little effect on blood pressure in the DOCA hypertensive rat. Methysergide is known to be useful in the treatment of migraine and produces a selective increase in carotid vascular resistance in the anaesthetised dog; it has been suggested (P. R. Saxena., Eur. J. Pharmacol, 1974, 27, 99–105) that this is the basis of its efficacy. Those compounds which we have tested show a similar effect in the anaesthetised dog and the compounds according to the invention are thus potentially useful for the treatment of migraine.

Accordingly, the invention also provides a pharmaceutical composition adapted for use in human medicine which comprises at least one compound of formula (I), a physiologically acceptable salt, solvate (e.g. hydrate) or bioprecursor thereof and formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); nonaqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The compounds of the invention may be formulated for parenteral administration by injection, including using conventional catheterisation techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for oral, parenteral or buccal administration to man for the treatment of migraine is 0.1 to 100 mg of the active ingredient per unit dose which could be administered, for example 1 to 4 times per day.

Aerosol formulations are preferably arranged so that each metered dose or 'puff' of aerosol contains 20 μg–1000 μg of a compound of the invention. The overall daily dose with an aerosol will be within the range 100 μg–10 mg. Administration may be several times daily, for example 2, 3, 4 or 8 times, giving for example 1, 2 or 3 doses each time. The overall daily dose and the metered dose delivered by capsules and cartridges in an inhaler or insufflator could be double those with aerosol formulations.

A preferred class of compounds represented by the general formula (I) is that in which $R_1$ represents an alkyl group containing 1 to 3 carbon atoms which may be unsubstituted or substituted by one to three fluorine atoms. Another preferred class of compounds is that where $R_2$ represents a hydrogen atom or a methyl group and $R_3$ represents a hydrogen atom.

A further preferred class of compounds represented by the general formula (I) is that wherein Alk represents an unsubstituted alkylene chain containing two carbon atoms. A still further preferred class of compounds is that in which $R_4$ and $R_5$, which may be the same or different, each represents a hydrogen atom or a methyl or ethyl group and $R_6$ and $R_7$ each represents a hydrogen atom. It is preferred that the total number of carbon atoms in $R_4$ and $R_5$ together does not exceed two.

A preferred class of compounds according to the invention is that represented by the general formula (Ia):

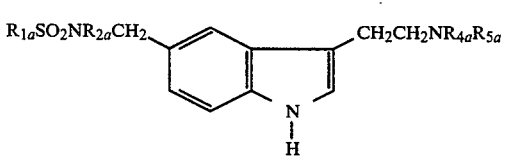

wherein
$R_{1a}$ represents an alkyl group containing 1 to 3 carbon atoms, e.g. methyl, or a trifluoromethyl group;
$R_{2a}$ represents a hydrogen atom or a methyl group; and
$R_{4a}$ and $R_{5a}$, which may be the same or different, each represents a hydrogen atom or a methyl or ethyl group,
and physiologically acceptable salts, solvates (e.g. hydrates) and bioprecursors thereof.

A particularly preferred class of compounds according to the invention is that represented by the general formula (Ib):

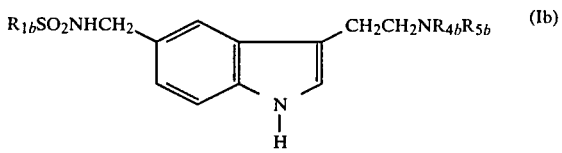

wherein
$R_{1b}$ represents an alkyl group containing 1 to 3 carbon atoms, e.g. methyl; and
$R_{4b}$ and $R_{5b}$, which may be the same or different, each represents a hydrogen atom or a methyl or ethyl group, such that the total number of carbon atoms in $R_{4b}$ and $R_{5b}$ together does not exceed two, and
physiologically acceptable salts, solvates (e.g. hydrates) and bioprecursors thereof.

Particularly preferred compounds according to the invention are N-[[3-[2-(methylamino)ethyl]-1H-indol-5-yl]methyl]methanesulphonamide and N-[[3-[2-(dimethylamino)ethyl]-1H-indol-5-yl]methyl]methanesulphonamide and physiologically acceptable salts, solvates (e.g. hydrates) and bioprecursors thereof.

According to another aspect of the invention, compounds of general formula (I) and physiologically acceptable salts, solvates (e.g. hydrates) or bioprecursors thereof, may be prepared by the general methods outlined below. In the following processes, $R_1$, $R_2$, $R_3$, $R_4$, $R_5$, $R_6$, $R_7$ and Alk are as defined for the general formula (I) unless otherwise specified.

According to one general process (A), a compound of general formula (I) may be prepared by reacting a compound of general formula (II):

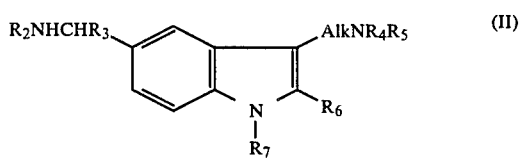

or a salt thereof (for example, an organic or inorganic acid addition salt such as the hydrochloride, hydrobromide, maleate, sulphate or creatinine sulphate adduct) or a protected derivative thereof, with a sulphonylating agent.

Suitable sulphonylating agents corresponding to the acid $R_1SO_3H$ include sulphonyl halides, for example sulphonyl chlorides ($R_1SO_2Cl$) and sulphonic anhydrides.

Particularly in the case of sulphonyl halides and acid anhydrides, the reaction may conveniently be carried out in the presence of a base such as pyridine or a tertiary amine such as triethylamine optionally in the presence of an inert organic solvent, at a temperature of from −70° to +100° C., preferably −5° to +50° C. The base may also serve as a reaction solvent. Suitable inert organic solvents include amides, such as N,N-dimethylformamide and ethers, such as tetrahydrofuran or mixtures thereof. The reaction may also be carried out in a two-phase system such as ethyl acetate and aqueous sodium hydrogen carbonate.

Some starting compounds of general formula (II) wherein $R_2$ is hydrogen, may be prepared by reduction of a corresponding compound having an appropriate reducible group as the 5-position substituent, such as —CN or

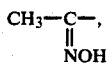

using for example lithium aluminium hydride.

According to another process (B), compounds of general formula (I) may be prepared by cyclisation of compounds of general formula (III):

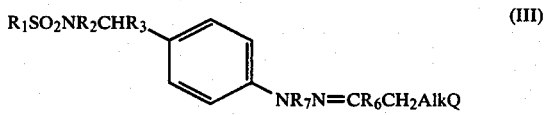

(wherein Q is the group $NR_4R_5$ or a protected derivative thereof, or a leaving group such as halogen (e.g. chlorine), acetate, tosylate or mesylate).

Suitable cyclisation methods are referred to in "A Chemistry of Heterocyclic Compounds—Indoles Part I", Chapter II, edited by W. J. Houlihan (1972) Wiley Interscience, New York. Particularly convenient embodiments of the process are described below.

When Q is the group $NR_4R_5$ (or a protected derivative thereof), to process is desirably carried out in an aqueous reaction medium, such as an aqueous alcohol (for example methanol) in the presence of an acid catalyst. (In some cases the acid catalyst may also act as the reaction solvent). Suitable acid catalysts include inorganic acids such as sulphuric or hydrochloric acid, organic carboxylic acids such as acetic acid. Alternatively the cyclisation may be carried out using a Lewis acid such as zinc chloride in ethanol or boron trifluoride in acetic acid. The reaction may conveniently be carried out at temperatures of from 20° to 200° C., preferably 50° to 125° C.

When Q is a leaving group, such as chlorine the reaction may be effected in an aqueous organic solvent, such as an aqueous alcohol (e.g. methanol, ethanol or isopropanol), in the absence of a mineral acid, conveniently at a temperature of from 20° to 200° C., preferably 50° to 125° C. This process results in the formation of a compound of formula (I) wherein $R_4$ and $R_5$ are both hydrogen atoms.

According to a particular embodiment of this process, compounds of general formula (I) may be prepared directly by the reaction of a compound of general formula (IV):

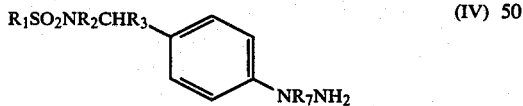

or a salt thereof, with a compound of formula (V):

$R_6COCH_2AlkQ$  (V)

(wherein Q is as defined above) or a salt or protected derivative thereof (such as an acetal or ketal e.g. formed with an appropriate alkylorthoformate), using the appropriate conditions as described above.

Compounds of general formula (III) may be isolated as intermediates during the process for the preparation of compounds of general formula (I) wherein a compound of formula (IV), or a salt or protected derivative thereof, is reacted with a compound of formula (V) or a salt or protected derivative thereof, in a suitable solvent, such as an aqueous alcohol (e.g. methanol) and at a temperature of, for example, from 20° to 30° C. If an acetal or ketal of a compound of formula (V) is used it may be necessary to carry out the reaction in the presence of an acid (for example, acetic or hydrochloric acid).

As illustrated in the following general processes (C) and (D), the aminoalkyl substituent $-AlkNR_4R_5$ may be introduced at the 3-position by a variety of conventional techniques which may, for example, involve modification of a substituent at the 3-position or direct introduction of the aminoalkyl substituent into the 3-position.

Thus a further general process (C) for preparing compounds of general formula (I) involves reacting a compound of general formula (VI):

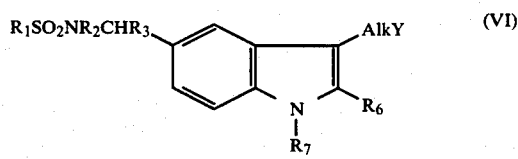

(wherein Y is a readily displaceable group) or a protected derivative thereof, with a compound of formula $R_4R_5NH$.

This displacement reaction may conveniently be carried out on those compounds of formula (VI) wherein the substituent group Y is a halogen atom (e.g. chlorine, bromine or iodine) or a group OR where OR is, for example, an acyloxy group, such as acetoxy, chloroacetoxy, dichloroacetoxy, trifluoroacetoxy or p-nitrobenzoyloxy or a sulphonate group (e.g. p-toluene sulphonate).

The above reaction is conveniently effected in an organic solvent (optionally in the presence of water), examples of which include alcohols, e.g. ethanol; ethers, e.g. tetrahydrofuran; esters e.g. ethyl acetate; amides e.g. N,N-dimethylformamide; and ketones e.g. acetone, at a temperature of from $-10°$ to $+150°$ C., preferably 20° to 50° C.

The compounds of formula (VI) wherein Y is a halogen atom may be prepared by reacting a hydrazine of formula (IV) with an aldehyde or ketone (or a protected derivative thereof) of formula (V) in which Q is a halogen atom, in an aqueous alkanol (e.g. methanol) containing an acid (e.g. acetic or hydrochloric acid) or by heating a compound of formula (VI) wherein Y is a hydroxy group with the appropriate phosphorus trihalide. The intermediate alcohol where Y is a hydroxy group may also be used to prepare compounds of formula (VI) wherein Y is the group OR by acylation or sulphonylation with the appropriate activated species (e.g. an anhydride or sulphonyl chloride) using conventional techniques.

Compounds of general formula (I) may also be prepared by another general process (D) involving reduction of a compound of general formula (VII):

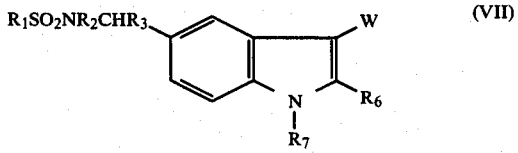

(wherein W is a group capable of being reduced to give the required AlkNR$_4$R$_5$ group or a protected derivative thereof) or a salt or protected derivative thereof.

The required Alk and NR$_4$R$_5$ groups may be formed by reduction steps which take place separately or together in any appropriate manner.

Groups which may be reduced to the group Alk include corresponding unsaturated groups and corresponding groups containing one or two carbonyl functions or a hydroxyl group.

Groups which may be reduced to the group NR$_4$R$_5$ where R$_4$ and R$_5$ are both hydrogen include nitro, azido, hydroxyimino and nitrile groups. Reduction of a nitrile group yields the group CH$_2$NH$_2$ and thus provides a methylene group of the group Alk.

The required NR$_4$R$_5$ group wherein R$_4$ and/or R$_5$ are other than hydrogen may be prepared by reduction of a nitrile (CHR$_8$)$_x$CHR$_9$CN or an aldehyde (CHR$_8$)$_x$CHR$_9$CHO (where R$_8$ and R$_9$, which may be the same or different each represents a hydrogen atom or a C$_{1-3}$ alkyl group) in the presence of an amine, R$_4$R$_5$NH. Alternatively the NR$_4$R$_5$ group may be prepared by reaction of the corresponding compound wherein R$_4$ and/or R$_5$ represent hydrogen with an appropriate aldehyde or ketone in the presence of a suitable reducing agent. In some instances (e.g. for the introduction of the group R$_5$ where R$_5$ is benzyl) the aldehyde (e.g. benzaldehyde) may be condensed with the amine and the intermediate thus formed may subsequently be reduced using a suitable reducing agent.

The required NR$_4$R$_5$ group wherein R$_4$ and/or R$_5$ are other than hydrogen may also be prepared by reduction of a corresponding amide, for example, AlkNR$_4$COR$_5^1$ (where R$_5^1$ is part of the group R$_5$ or the group OR$^a$ where R$^a$ is an alkyl or aralkyl group).

Examples of groups represented by the substituent group W include the following:

TNO$_2$ (where T is Alk or an alkenyl group corresponding to the group Alk); AlkN$_3$; AlkNR$_4$COR$_5^1$; —COCONR$_4$R$_5$; (CHR$_8$)$_x$CHR$_9$CN; CHR$_9$COZ; (CHR$_8$)$_x$CR$_9$=NOH; CH(OH)CHR$_9$NR$_4$R$_5$; COCHR$_9$Z (where R$_8$ and R$_9$ are as previously defined, Z is an azido group N$_3$ or the group NR$_4$R$_5$ or a protected derivative thereof and x is zero or 1).

It will be appreciated that the choice of reducing agent and reaction conditions will be dependent on the nature of the group W.

Suitable reducing agents which may be used in the above process include hydrogen in the presence of a metal catalyst (except when W contains an amide group), an alkali metal borohydride or cyanoborohydride, e.g. sodium borohydride or cyanoborohydride (except, in general, when W contains an amide, nitrile or hydroxyimino group) or a metal hydride, e.g. lithium aluminium hydride (except, in general, when W contains a nitrile group and the reduction is carried out in the presence of an amine HNR$_4$R$_5$).

The metal catalyst may be, for example, Raney Nickel or a noble metal catalyst, such as platinum, platinum oxide, palladium or rhodium, which may be supported, for example, on charcoal or kieselguhr. In the case of Raney nickel, hydrazine may also be used as the source of hydrogen.

Reduction in the presence of hydrogen and a metal catalyst may conveniently be carried out in a solvent such as an alcohol e.g. ethanol, an ether e.g. dioxan or tetrahydrofuran, or an ester e.g. ethyl acetate at a temperature of from $-10°$ to $+50°$ C., preferably $-5°$ to $+30°$ C. The alkali metal borohydride or cyanoborohydride reduction may conveniently be carried out in an alcohol such as propanol or ethanol and at a temperature of from 10° to 100° C. The metal hydride reduction may be carried out using an ether, e.g. tetrahydrofuran as solvent, and conveniently at a temperature of from $-10°$ to $+100°$ C. In some instances the reduction using borohydride may be carried out in the presence of cobaltous chloride.

A particular embodiment of this process includes the reduction of a compound of formula (VII) wherein W is the group CHR$_9$CN, CHR$_8$CHR$_9$NO$_2$, CH=CR$_9$NO$_2$ or CHR$_8$CR$_9$=NOH using, for example, lithium aluminium hydride or by catalytic reduction with hydrogen, e.g. hydrogen in the presence of a catalyst such as palladium, optionally in the presence of a mineral acid, such as hydrochloric or sulphuric acid.

A second embodiment of the process involves, for example, the reduction of a compound of formula (VII) wherein W is the group CHR$_9$CN in the presence of an amine HNR$_4$R$_5$ using hydrogen in the presence of a catalyst such as palladium.

A third embodiment of the process involves the reduction using, for example, lithium aluminium hydride, of a compound of formula (VII) wherein W is the group —COCONR$_4$R$_5$, CHR$_9$CONR$_4$R$_5$ or AlkNR$_4$COR$_5^1$. A particular example of this process is reduction of a compound of formula (VII) wherein W is the group AlkNR$_4$CO$_2$CH$_2$Ph, using for example lithium aluminium hydride to give a compound of formula (I) wherein R$_5$ is a methyl group.

According to a fourth embodiment, a compound of formula (VII) wherein W is a group COCHR$_9$Z may be reduced preferably with heating, using, for example, sodium borohydride in propanol. Where Z is an azido group, the process results in the formation of a compound of formula (I) wherein R$_4$ and R$_5$ are both hydrogen atoms.

According to a fifth embodiment, a compound of formula (VII) wherein W is the group AlkN$_3$ or CH(OH)CHR$_9$NR$_4$R$_5$ may be reduced using for example hydrogen in the presence of a catalyst such as palladium, lithium aluminium hydride or sodium borohydride. These reducing agents are also suitable for the reductive alkylation of, for example, AlkNHR$_4$ in the presence of a suitable aldehyde or ketone.

The starting materials or intermediate compounds of general formula (VII) may be prepared by analogous methods to those described in UK Published Patent Application No. 2035310 and "A Chemistry of Heterocyclic Compounds—Indoles Part II" Chapter VI edited by W. J. Houlihan (1972) Wiley Interscience, New York.

Compounds of formula (VII) wherein W is the group —COCONR$_4$R$_5$ may be prepared by treating the corresponding 3-unsubstituted derivative with oxalyl chloride followed by treatment with a compound of formula HNR$_4$R$_5$.

Compounds of formula (VII) wherein W is the group (CHR$_8$)$_x$CHR$_9$CHO may be prepared by oxidation (e.g. with Jones' reagent) of a compound of formula (VI) wherein Y is a hydroxyl group. A compound of formula (VII) wherein W is the group (CHR$_8$)$_x$CR$_9$=NOH may be prepared by treatment of the corresponding aldehyde with hydroxylamine hydrochloride using standard conditions.

The intermediate compound of formula (VII) wherein W is the group AlkN$_3$ may be prepared from a compound of formula (VI) wherein Y is a halogen atom using standard procedures.

A compound of formula (VII) wherein W is the group AlkNHCOR$_5^1$ may be prepared by acylation of the corresponding unsubstituted amine using conventional techniques.

The Fischer-indole cyclisation process may be employed to prepare a compound of formula (VII) wherein W is the group (CHR$_8$)$_x$CHR$_9$CO alk (where alk is a C$_{1-3}$ alkyl group) which may be converted into the corresponding azide, amide or alcohol using conventional techniques.

The standard reducing agents such as sodium borohydride may be used to prepare a compound of formula (VII) wherein W is the group CH(OH)CHR$_9$NR$_4$R$_5$ from the corresponding compound of formula (VII) wherein W is the group COCHR$_9$NR$_4$R$_5$.

Compounds of formula (I) may also be prepared by a fifth general process (E) comprising the decarboxylation of a compound of general formula (VIII):

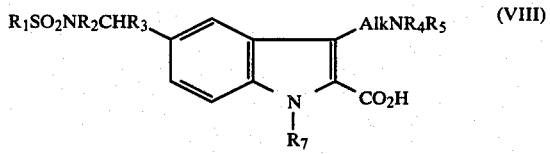

or a salt or protected derivative thereof.

The decarboxylation may be effected by heating a compound of the formula (VIII) or a salt or protected derivative thereof, at a temperature of from 30° to 150° C., preferably 50° to 120° C., in the presence of an acid such as acetic acid or hydrochloric acid or a mixture thereof.

Compounds of general formula (VIII) may be obtained by hydrolysis of a compound of formula (IX):

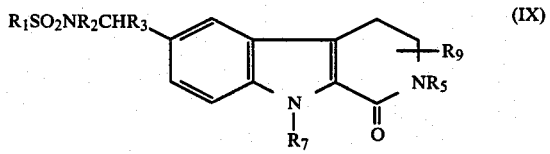

wherein R$_9$ is as previously defined above or a protected derivative thereof.

The following reactions (F), in any appropriate sequence, may if necessary and/or desired, be carried out subsequent to any of the above described processes:
(i) conversion of one compound of general formula (I) or a salt or protected derivative thereof into another compound of general formula (I);
(ii) removal of any protecting groups; and
(iii) conversion of a compound of general formula (I) or a salt thereof into a physiologically acceptable salt, solvate (e.g. hydrate) or bioprecursor thereof.

Thus, a compound of formula (I) according to the invention may be converted into another compound of the invention using conventional procedures.

For example, a compound of general formula (I) wherein one or more of R$_2$, R$_4$, R$_5$ and R$_7$ are alkyl groups may be prepared from the corresponding compounds of formular (I) wherein one or more of R$_2$, R$_4$, R$_5$ and R$_7$ represent hydrogen atoms, by reaction with a suitable alkylating agent such as an alkyl halide, alkyl tosylate or dialkylsulphate. The alkylation reaction is conveniently carried out in an inert organic solvent such as an amide (e.g. dimethylformamide) an ether (e.g. tetrahydrofuran) or an aromatic hydrocarbon (e.g. toluene) preferably in the presence of a base. Suitable bases include, for example, alkali metal hydrides, such as sodium hydride, alkali metal amides, such as sodium amide, alkali metal carbonates, such as sodium carbonate or alkali metal alkoxides such as sodium or potassium methoxide, ethoxide or t-butoxide.

A particularly suitable method for preparing a compound of formula (I) wherein R$_4$ and/or R$_5$ is other than hydrogen, is reductive alkylation of the corresponding compound wherein R$_4$ and/or R$_5$ represents hydrogen, with an appropriate aldehyde or a ketone (e.g. benzaldehyde or acetone) in the presence of a suitable reducing agent. Alternatively the aldehyde or ketone may be condensed with the primary amine and the intermediate thus formed may subsequently be reduced using a suitable reducing agent. It will be appreciated that the choice of reducing agents and reaction conditions depends upon the nature of the substituent groups already present on the compound of formula (I) which is to be alkylated. Suitable reducing agents which may be employed in this reaction include hydrogen in the presence of a metal catalyst, an alkali metal borohydride or cyanoborohydride (e.g. sodium borohydride or cyanoborohydride) using the conditions previously described or formic acid (using the carbonyl compound as reaction solvent, at a temperature of from 0°–100° C., conveniently 0°–50° C.).

According to a further embodiment, a compound of general formula (I) where R$_5$ is a hydrogen atom, may be prepared by reduction of a corresponding compound of general formula (I) wherein R$_5$ is a benzyl group, for example with hydrogen in the presence of a catalyst e.g. 10% palladium on carbon.

It should be appreciated that in some of the above transformations it may be necessary or desirable to protect any sensitive groups in the molecule of the compound in question to avoid undesirable side reactions. For example, during any of the reaction sequences described above, it may be necessary to protect the group NR$_4$R$_5$, wherein R$_4$ and/or R$_5$ represent hydrogen, with a group easily removable at the end of the reaction sequence. Such groups may include, for example, aralkyl groups, such as benzyl, diphenylmethyl or triphenymethyl; or acyl groups, such as N-benzyloxycarbonyl or t-butoxycarbonyl or phthaloyl.

In some cases, it may also be necessary to protect the indole nitrogen wherein R$_7$ is hydrogen.

Subsequent cleavage of the protecting group may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

Where it is desired to isolate a compound of the invention as a salt, for example as an acid addition salt, this may be achieved by treating the free base of general formula (I), with an appropriate acid, preferably with an equivalent amount or with creatinine sulphate in a suitable solvent (e.g. aqueous ethanol).

The starting materials or intermediate compounds for the preparation of the compounds according to this invention may be prepared by analogous methods to those described in UK Published Patent Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced either before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following Examples. All temperatures are in °C.

PREPARATION 1

2-[2-[5-(Aminomethyl)-1H-indol-3-yl]ethyl]-1H-isoindole-1,3(2H)-dione, hemisulphate, hydrate A suspension of 3-[2-(1,3-dihydro-1,3-dioxo-2H-isoindol-2-yl)ethyl]-1H-indole-5-carbonitrile (4.7 g) in methanol (250 ml) and sulphuric acid (1.5 ml) was hydrogenated at room temperature and pressure over 10% palladium on charcoal (50% aqueous paste; 2.0 g) for 45 h. The catalyst was filtered off, and the filtrate was evaporated to dryness, giving an orange oil, which was dissolved in hot water (70 ml). On cooling, the title compound crystallised as a cream solid (3.8 g) m.p. 235°–8°.

PREPARATION 2

N-[(1H-indol-5-yl)methyl]methanesulphonamide (i) 1H-Indole-5-methanamine

A solution of 1H-indole-5-carbonitrile (3.7 g) in tetrahydrofuran (25 ml) was added over fifteen minutes to a stirred suspension of lithium aluminium hydride (3.1 g) in tetrahydrofuran (80 ml) under nitrogen. After thirty minutes, the suspension was heated at reflux for two hours. After cooling to 0°, water (3.1 ml), sodium hydroxide (2N, 6.2 ml) and water (9.3 ml) were added with caution, the resulting salts were filtered off and the filtrate was concentrated under vacuum to afford a yellow oil (3.3 g) which was crystallised from ethyl acetate to give the title compound as a pale cream solid m.p. 114°–5°.

(ii) N-[(1H-Indol-5-yl)methyl]methanesulphonamide

Methanesulphonyl chloride (1.63 ml) was added dropwise to a stirred solution of 1H-indole-5-methanamine (2.1 g) in pyridine (25 ml) at 0°. After 30 minutes the red solution was poured into water (50 ml) and extracted with ethyl acetate (3×50 ml). The combined organic extracts were washed with hydrochloric acid (2N, 4×50 ml), brine (30%, 3×40 ml) dried and concentrated under vacuum to afford a red oil (1.9 g). Column chromatography (Kieselgel G, 20 g) with ether as eluant afforded the title sulphonamide (1.62 g) as a pale red solid, m.p. 122°–124°.

PREPARATION 3

Phenylmethyl[2-[5-(aminomethyl)-1H-indol-3-yl]ethyl]carbamate (i)

Phenylmethyl[2-[5-(hydroxymethyl)-1H-indol-3-yl]ethyl]carbamate

A solution of 3-[2-[[(phenylmethoxy)carbonyl]amino]ethyl]-1H-indole-5-carboxylic acid (9 g) and carbonyldiimidazole (5.2 g) in dry tetrahydrofuran (THF) (150 ml) was stirred vigorously under nitrogen at room temperature for 5 h. A solution of lithium borohydride (1.6 g) in dry THF (70 ml) was added over 70 min and the mixture was then stirred for 18 h.

Aqueous acetic acid (30%, 25 ml) was added slowly to the ice-cooled mixture and the solution was then partitioned between brine (25%, 300 ml) and ethyl acetate (250 ml). The organic layer was washed with sulphuric acid (0.4M, saturated with sodium chloride, 3×80 ml), brine (100 ml) and potassium carbonate solution (25%, 2×100 ml). The dried (MgSO$_4$) solution was evaporated in vacuo, the residue taken up in dichloromethane (150 ml) and insoluble material was filtered off. The filtrate was evaporated in vacuo to leave the alcohol (9 g) as a colourless oil containing some (ca. 45 mole %) ethyl acetate, T.L.C. SiO$_2$/Et$_2$O, Rf 0.25.

(ii)

Phenylmethyl[2-[5-(aminomethyl)-1H-indol-3-yl]ethyl]carbamate

A solution of diethyl azodicarboxylate (1.48 g) in dry tetrahydrofuran (THF) (8 ml) was added over 2 min., keeping the temperature at 25°, to a stirred solution of phenylmethyl[2-[5-(hydroxymethyl)-1H-indol-3-yl]ethyl]carbamate (2.6 g), triphenylphosphine (2.35 g) and phthalimide (1.75 g) in THF (20 ml). After 4 h, the solvent was evaporated in vacuo and the residue was dissolved in a solution of hydrazine hydrate (15 ml) in ethanol (100 ml).

After 5 days the mixture was partitioned between sulphuric acid (0.5N, 500 ml) and ethyl acetate (2×300 ml). The acid layer was basified with potassium carbonate and the product was extracted into ethyl acetate (200 ml). The dried (Na$_2$SO$_4$) extract was evaporated in vacuo to leave the crude amine (0.7 g) as a brown oil which later solidified. Crystallisation from ethyl acetate gave the title compound (0.15 g) as cream coloured crystals m.p. 123.5°–126.5°.

EXAMPLE 1

N-[[3-(2-Aminoethyl)-1H-indol-5-yl]methyl]methanesulphonamide, compound with creatinine, sulphuric acid and water (1:1:1:1)

(i)

N-[[3-[2-(1,3-Dihydro-1,3-dioxo-2H-isoindol-2-yl)ethyl]-1H-indol-5-yl]methyl]methanesulphonamide Methanesulphonyl chloride (0.23 ml) was added to an ice cooled, stirred solution of 2-[2-[5-(aminomethyl)-1H-indol-3-yl]ethyl]-1H-isoindole-1,3(2H)-dione, hemisulphate, hydrate (0.84 g) in dry pyridine (25 ml). After 20 h at room temperature, a further portion of methanesulphonyl chloride (0.14 ml) was added. The mixture was stirred for 2 h, water (10 ml) was added and the solution was stirred for a further 1 h. The solution was diluted with hydrochloric acid (2N; 250 ml) containing sodium chloride (30 g) and ice. The product was extracted into ethyl acetate (2×80 ml) and the extract was washed with brine (2×60 ml), dried (Na$_2$SO$_4$) and evaporated in vacuo to leave a yellow foam (0.85 g).

A sample (0.65 g) was crystallised from ethyl acetate to give the title compound as yellow crystals (0.43 g) m.p. 162.5°-165°.

(ii)
N-[[3-(2-Aminoethyl)-1H-indol-5-yl]methyl]methanesulphonamide, compound with creatinine, sulphuric acid and water (1:1:1:1)

A solution of N-[[3-[2-(1,3-dihydro-1,3-dioxo-2H-isoindol-2-yl)ethyl]-1H-indol-5-yl]methyl]methanesulphonamide (0.95 g) in ethanolic methylamine (33%; 40 ml) was kept at room temperature for 2.5 h. The solvent was evaporated in vacuo and the residue was re-evaporated with ethanol (2×50 ml). The residue was dissolved in hot ethanol (100 ml) and an aqueous solution of creatinine and sulphuric acid (1:1; 2M; 1.25 ml) was added, followed by ethanol (50 ml). Filtration of the cooled solution gave the title compound (0.6 g) as a cream solid m.p. 215°-8°.

Analysis Found: C, 38.5; H, 5.4; N, 16.8; C$_{12}$H$_{17}$N$_3$O$_2$S.C$_4$H$_7$N$_3$O.H$_2$SO$_4$.H$_2$O requires: C, 38.7; H, 5.7; N, 16.95%.

EXAMPLE 2

N-[[3-[2-(Methylamino)]ethyl-1H-indol-5-yl]methyl]methanesulphonamide, maleate (i)
N-[2-[5-[[(Methylsulphonyl)amino]methyl]1H-indol-3-yl]ethyl]formamide A solution of N-[[3-(2-aminoethyl)-1H-indol-5-yl]methyl]methanesulphonamide (2.1 g) in ethanol (20 ml) and ethyl formate (25 ml) was refluxed for 17 h. The solvent was evaporated in vacuo and the residue was partitioned between sulphuric acid (1N; 100 ml) and ethyl acetate (150 ml). The aqueous layer was extracted with ethyl acetate (150 ml) and the combined organic extracts were washed with brine (50 ml) and potassium carbonate solution (15%; 50 ml) and dried (Na$_2$SO$_4$). Evaporation of the solvent in vacuo gave the crude product as a very viscous oil (2.2 g). The oil was dissolved in THF (8 ml), scratched and left overnight at room temperature. Filtration gave the title compound (1.3 g) as a white solid m.p. 121°-5°.

(ii)
N-[[3-[2-(Methylamino)ethyl]-1H-indol-5-yl]methyl]methanesulphonamide, maleate A solution of N-[2-[5-[[(methylsulphonyl)amino]methyl]-1H-indol-3-yl]ethyl]formamide (0.43 g) in dry tetrahydrofuran (THF) (20 ml) was added over 5 min under nitrogen, to a stirred suspension of lithium aluminium hydride (0.5 g) in dry THF (14 ml). The mixture was then refluxed for 4½ h. The mixture was cooled in ice and excess reagent was decomposed by cautious addition of 10% water in THF. Brine (50 ml) and ethyl acetate (100 ml) were added, insoluble material filtered off and the aqueous layer extracted with ethyl acetate (2×100 ml). The combined organic solutions were washed with brine (50 ml), dried (Na$_2$SO$_4$) and evaporated in vacuo to leave an almost colourless oil. The oil was dissolved in a solution of maleic acid (0.6 g) in methanol (6 ml) and the maleate was precipitated by the addition of ethyl acetate (15 ml) and ether (120 ml).

The salt was crystallised twice from a mixture of methanol and ethyl acetate to give the title compound (0.16 g) as fawn crystals m.p. 140°-141.5°.

Analysis Found: C, 51.0; H, 5.8; N, 10.2; C$_{13}$H$_{19}$N$_3$O$_2$S.C$_4$H$_4$O$_4$ requires: C, 51.4; H, 5.8; N, 10.6%.

EXAMPLE 3

N-[[3-[2-(Dimethylamino)ethyl]-1H-indol-5-yl]methyl]methanesulphonamide, maleate (i)
Phenylmethyl[2-[5-[[(methylsulphonyl)amino]methyl]-1H-indol-3-yl]ethyl](methyl)carbamate Benzyl chloroformate (1.1 ml) was added to a stirred, ice-cooled solution of N-[[3-[2-(methylamino)ethyl]-1H-indol-5-yl]methyl]methanesulphonamide (1.3 g) and diisopropylethylamine (1.5 ml) in dry THF (40 ml). After ½ h, water (3 ml) was added and the stirring was continued for 1 h.

The mixture was partitioned between ethyl acetate (50 ml) and sulphuric acid (1N; 50 ml; containing 8 g sodium chloride) and the aqueous layer was extracted with ethyl acetate (50 ml). The combined organic extracts were washed with brine (30 ml) and potassium carbonate solution (20%; 30 ml), dried (Na$_2$SO$_4$) and evaporated in vacuo to leave a brown oil (2.7 g). Crystallization twice from ethyl acetate gave the title compound (0.85 g) m.p. 118.5°-120°.

(ii)
N-[[3-[2-(Dimethylamino)ethyl]-1H-indole-5-yl]methyl]methanesulphonamide, maleate A solution of phenylmethyl[2-[5-[[(methylsulphonyl)amino]methyl]-1H-indol-3-yl]ethyl](methyl)carbamate (0.4 g) in dry THF (16 ml) was added, over 5 min, under nitrogen, to a stirred suspension of lithium aluminium hydride (0.5 g) in dry THF (20 ml). After 1 h at room temperature, the mixture was refluxed for 3 h, cooled in ice and the excess reagent was decomposed by the addition of 10% water in THF (ca 25 ml). Water (25 ml), sodium chloride (5 g) and ethyl acetate (30 ml) were added and the mixture was stirred for 10 min. Insoluble material was filtered off and the aqueous layer was extracted with ethyl acetate (2×50 ml). The combined organic extracts were dried (Na$_2$SO$_4$) and evaporated in vacuo to leave a pale green oil (0.35 g). The oil was dissolved in a solution of maleic acid (0.25 g) in methanol (5 ml) and the maleate was precipitated by the addition of ethyl acetate (30 ml) and ether (130 ml).

Crystallisation from a mixture of methanol and ethyl acetate gave the title compound (0.33 g) as off-white crystals m.p. 136°-137.5°.

Analysis Found: C, 52.6; H, 6.1; N, 10.0; C$_{14}$H$_{21}$N$_3$O$_2$S.C$_4$H$_4$O$_4$ requires: C, 52.5; H, 6.1; N, 10.2%.

EXAMPLE 4

N-[[3-[2-(Methylamino)ethyl]-1H-indol-5-yl]methyl]methanesulphonamide

A solution of phenylmethyl[2-[5-[[(methylsulphonyl)amino]methyl]-1H-indol-3-yl]ethyl]carbamate (0.02 g) in dry THF (1 ml) was added to a stirred suspension of lithium aluminium hydride (0.1 g) in THF (2 ml) and the mixture was refluxed under nitrogen for 3 h. The mixture was cooled and excess reagent was decomposed by the addition of 10% water in THF. Salt and ethyl acetate (20 ml) were added and the organic layer was dried (Na$_2$SO$_4$) and evaporated in vacuo to leave the title compound as a brown oil (0.015 g).

TLC silica, ethyl acetate, 2-propanol, water, 0.88 ammonia (25:15:8:2) R$_f$ 0.4 identical to an authentic sample (see Example 2).

EXAMPLE 5

N-[[3-[2-(Ethylamino)ethyl]-1H-indol-5-yl]methyl]methanesulphonamide, maleate (i)

N-[2-[5-[[(Methylsulphonyl)amino]methyl]-1H-indol-3-yl]ethyl]acetamide

Acetic anhydride (1.0 ml) was added to a solution of N-[[3-(2-aminoethyl)-1H-indole-5-yl]methyl]methanesulphonamide (1.5 g) in 8% sodium bicarbonate (50 ml) and ethyl acetate (50 ml). The two phase mixture was stirred at room temperature for 2 h. The layers were separated and the aqueous layer was extracted with ethyl acetate (2×50 ml). The organic extracts were dried and evaporated to give a brown oil (1.93 g). Trituration with ethyl acetate (ca. 25 ml) yielded a fawn solid (1.15 g). Crystallisation from a mixture of the methanol (5 ml) and ethyl acetate (18 ml) gave the title amide as cream crystals (0.58 g) m.p. 129°–130°.

(ii)

N-[[3-[2-(Ethylamino)ethyl]-1H-indol-5-yl]methyl]methanesulphonamide, maleate

A solution of N-[2-[5-[[(methylsulphonyl)amino]methyl]-1H-indol-3-yl]ethyl]acetamide (0.80 g) in dry THF (55 ml) was added dropwise over 20 min to an ice-cooled, stirred suspension of lithium aluminium hydride (0.4 g) in dry THF under nitrogen. The mixture was stirred under reflux for 12 h and then allowed to cool. Aqueous THF (15% H$_2$O; 10 ml) was added dropwise followed by water (20 ml). The mixture was saturated with sodium chloride and ethyl acetate (10 ml) was added. The layers were separated and the aqueous layer was extracted with ethyl acetate (2×15 ml). The combined organic extracts were dried (Na$_2$SO$_4$) and evaporated to give a brown oil (0.71 g).

The oil was dissolved in hot methanol (ca. 10 ml) and a solution of maleic acid (0.26 g) in hot methanol (ca. 1 ml) was added. On addition of ethyl acetate (ca. 35 ml) and cooling a pale brown solid crystallised (0.58 g). Recrystallisation from a mixture of methanol and ethyl acetate gave the title maleate as pale fawn crystals (0.45 g) m.p. 160°–161°.

Analysis Found: C, 52.7; H, 6.1; N, 10.0; C$_{14}$H$_{21}$N$_3$O$_2$S.C$_4$H$_4$O$_4$ requires: C, 52.5; H, 6.1; N, 10.2%.

EXAMPLE 6

N-[[3-(2-Aminoethyl)-1H-indol-5-yl]methyl]methanesulphonamide, compound with creatinine, sulphuric acid and water (1:1:1:1)

(i)

Phenylmethyl[2-[5-[[(Methylsulphonyl)amino]methyl]-1H-indol-3-yl]ethyl]carbamate Methanesulphonyl chloride (0.3 ml) was added in 3 portions over 3 h to a stirred, ice-cold solution of phenylmethyl[2-[5-(aminomethyl)-1H-indol-3-yl]ethyl]carbamate (0.45 g) in dry pyridine (15 ml). After a further 1 h, the mixture was partitioned between ice-cooled hydrochloric acid (1N, 300 ml) and ethyl acetate (200 ml). The organic layer was washed with brine (80 ml) and potassium carbonate solution (ca. 40%; 50 ml), dried (Na$_2$SO$_4$) and evaporated in vacuo to leave a yellow gum (0.45 g). Chromatography on silica gel (MFC: 18 g), eluting with increasing concentrations of ether in dichloromethane, gave the title compound (0.3 g) as an almost colourless oil.

Analysis Found: C, 59.3; H, 5.8; N, 9.9; C$_{20}$H$_{23}$N$_3$O$_4$S requires: C, 59.8; H, 5.8; N, 10.5%.

(ii)

N-[[3-(2-Aminoethyl)-1H-indol-5-yl]methyl]methanesulphonamide, compound with creatinine, sulphuric acid and water (1:1:1:1)

A solution of phenylmethyl [2-[5-[[(methylsulphonyl)amino]methyl]-1H-indol-3-yl]ethyl]carbamate (0.22 g) in ethanol (20 ml) was hydrogenated at room temperature and pressure over palladium oxide on charcoal (10%; pre-reduced, 0.2 g) until uptake of hydrogen ceased (12 minutes; 8 ml). The catalyst was filtered off and the filtrate was evaporated in vacuo to leave a pale yellow oil. The oil was dissolved in hot ethanol (12 ml) and water (0.1 ml) and an aqueous solution of creatinine and sulphuric acid (2M; 1:1; 0.26 ml) was added.

Filtration of the cooled mixture gave the title compound (0.175 g) as a white solid m.p. 215°–8°.

EXAMPLE 7

N-[[3-(2-Aminoethyl)-1H-indol-5-yl]methyl]trifluoromethanesulphonamide, compound with creatinine, sulphuric acid and water (1:1:1:1)

(i)

N-[[3-[2-(1,3-Dihydro-1,3-dioxo-2H-isoindol-2-yl)ethyl]-1H-indol-5-yl]methyl]trifluoromethanesulphonamide A suspension of 2-[2-(5-aminomethyl-1H-indol-3-yl)ethyl]-1H-isoindole-1,3(2H)-dione, hemisulphate, hydrate (1.10 g) in pyridine (40 ml) was cooled in an icebath and treated dropwise with trifluoromethanesulphonyl chloride (0.5 ml). The mixture was stirred at room temperature for 5.5 h, further trifluoromethanesulphonyl chloride (0.5 ml) being added after 4.75 h, and water (10 ml) was added. After 10 minutes the solution was acidified with hydrochloric acid (2N) and extracted into ethyl acetate (4×100 ml). The combined extract was washed with sodium carbonate (2N; 100 ml), dried (magnesium sulphate) and evaporated to dryness, affording a yellow-brown foam (1.2 g). This was purified by chromatography on a silica column (Merck Kieselgel 60; 22 g) eluted with ethyl acetate, affording title material as a yellow-brown solid (0.91 g), m.p. 176°–8°.

(ii)

N-[[3-(2-Aminoethyl)-1H-indol-5-yl]methyl]trifluoromethanesulphonamide, compound with creatinine, sulphuric acid and water (1:1:1:1)

A solution of N-[[3-[2-(1,3-dihydro-1,3-dioxo-2H-isoindol-2-yl)ethyl]-1H-indol-5-yl]methyl]trifluoromethanesulphonamide (0.59 g) in ethanol (90 ml) was treated with hydrazine hydrate (0.35 ml) and heated at reflux for 6 h. After cooling, the solution was evaporated to dryness, and the resulting white solid was partitioned between sodium carbonate solution (2N; 100 ml) and ethyl acetate (4×100 ml). The combined organic extract was dried (magnesium sulphate) and evaporated to dryness, affording an orange foam (0.45 g) which was purified by chromatography on a silica column (Merck Kieselgel 60; 15 g) eluted with methanol-ammonium hydroxide (66:1), affording pure title base as a pale yellow oil (0.28 g). This was dissolved in a hot mixture of ethanol (24 ml) and water (3 ml), and an aqueous solution of creatinine and sulphuric acid (1:1; 2M; 0.45 ml) was added. Filtration of the cooled solution gave the title compound (0.37 g) as white solid, m.p. 244°–6° (dec).

Analysis Found: C, 34.5; H, 4.5; N, 15.9%; $C_{12}H_{14}F_3N_3O_2S.C_4H_7N_3O.H_2SO_4.H_2O$ requires: C, 34.9; H, 4.6; N, 15.3%.

EXAMPLE 8

N-[[3-(2-Aminoethyl)-1H-indol-5-yl]methyl]phenylmethanesulphonamide, compound with creatinine, sulphuric acid and water (2:2:2:3)

(i)

N-[[3-[2-(1,3-Dihydro-1,3-dioxo-2H-isoindol-2-yl)ethyl]-1H-indol-5-yl]methyl]phenylmethanesulphonamide In a similar manner to that described in Example 7(i) 2-[[2-(5-aminomethyl)-1H-indol-3-yl]ethyl]-1H-isoindole-1,3(2H)-dione, hemisulphate, hydrate (1.01 g) and α-toluenesulphonyl chloride (0.99 g) in pyridine (40 ml) gave the title compound (0.58 g) as a yellow foam. T.L.C. silica, ethyl acetate $R_f$ 0.62.

(ii)

N-[[3-(2-Aminoethyl)-1H-indol-5-yl]methyl]phenylmethanesulphonamide, compound with creatinine, sulphuric acid and water (2:2:2:3)

In a similar manner to that described in Example 7(ii) N-[[3-[2-(1,3-dihydro-1,3-dioxo-2H-isoindol-2-yl)ethyl]-1H-indol-5-yl]methyl]phenylmethanesulphonamide (0.45 g) and hydrazine hydrate (0.5 ml) in ethanol (60 ml) gave the title compound (0.37 g) m.p. 214°–6°, without recourse to chromatography.

Analysis Found: C, 45.0; H, 5.4; N, 14.6; $C_{18}H_{21}N_3O_2S.C_4H_7N_3O.H_2SO_4.1.5H_2O$ requires: C, 45.4; H, 5.7; N, 14.45%.

EXAMPLE 9

N-[[3-(2-Aminoethyl)-1H-indol-5-yl]methyl]benzenesulphonamide, hemifumarate, hemihydrate (i)

N-[[3-[2-(1,3-Dihydro-1,3-dioxo-2H-isoindol-2-yl)ethyl]-1H-indol-5-yl-]methyl]benzenesulphonamide Benzenesulphonyl chloride (0.33 ml) was added to an ice-cooled, stirred solution of 2-[2-[5-(aminomethyl)-1H-indol-3-yl]ethyl]-1H-isoindole-1,3(2H)-dione, hemisulphate, hydrate (0.84 g) in dry pyridine (25 ml). After 2 h with ice cooling, the mixture was stirred at room temperature for 1 h. Water (5 ml) was added and the solution was stirred for 1 h. The mixture was diluted to 100 ml with water and the yellow solid (0.8 g) filtered off, m.p. 214°–6°.

A sample (0.1 g) was crystallised from methanol to give the title compound (0.06 g) as yellow crystals m.p. 225°–6°.

(ii)

N-[[3-(2-Aminoethyl)-1H-indol-5-yl]methyl]benzenesulphonamide, hemifumarate, hemihydrate A solution of N-[[3-[2-(1,3-dihydro-1,3-dioxo-2H-isoindol-2-yl)ethyl]-1H-indol-5-yl]methyl]benzenesulphonamide (0.7 g) in ethanolic methylamine (33%; 20 ml) was kept at room temperature for 3 h. The solvent was evaporated in vacuo and the residue was re-evaporated with ethanol (2×25 ml). The residue was dissolved in a warm solution of fumaric acid (0.22 g) in methanol (8 ml). Insoluble material was filtered off and ethyl acetate (20 ml) and ether (100 ml) were added to the filtrate. The precipitated gum was crystallised from a mixture of methanol and ethyl acetate to give, in two crops, pale yellow crystals (0.35 g) m.p. 212°–4°.

Recrystallisation from methanol gave the title compound as yellow crystals (0.17 g) m.p. 207°–9°.

Analysis Found: C, 57.55; H, 5.4; N, 10.4; $C_{17}H_{19}N_3O_2S.0.5C_4H_4O_4.0.5H_2O$ requires: C, 57.6; H, 5.55; N, 10.6%.

EXAMPLE 10

N-[[3-(2-Aminoethyl)-1H-indol-5-yl]methyl]-N-methylmethanesulphonamide, maleate (i)

N-[[3-[2-(1,3-Dihydro-1,3-dioxo-2H-isoindol-2-yl)ethyl]-1H-indol-5-yl]methyl]-N-methylmethanesulphonamide Sodium hydride (80% in oil; 0.1 g) was added under nitrogen to a stirred solution of N-[[3-[2-(1,3-dihydro-1,3-dioxo-2H-isoindol-2-yl)ethyl]-1H-indol-5-yl]methyl]methanesulphonamide (1.2 g) in dry dimethylformamide (16 ml). After 1 h, methyl iodide (0.75 ml) was added.

After a further 1 h at room temperature, the mixture was partitioned between brine (10%; 200 ml) and ethyl acetate (250 ml). The organic solution was washed with brine (2×100 ml), dried ($Na_2SO_4$) and evaporated in vacuo to leave a yellow oil (1.5 g).

Chromatography on silica gel (MFC: 100 g) eluting with chloroform, increasing to 10% ether in chloroform gave a pale yellow oil (1.0 g) which was crystallized from ethyl acetate/ether to give the title compound as a yellow crystalline solid (0.65 g) m.p. 166°–171°.

(ii)

N-[[3-(2-Aminoethyl)-1H-indol-5-yl]methyl]-N-methylmethanesulphonamide, maleate

A solution of N-[[3-[2-(1,3-dihydro-1,3-dioxo-2H-isoindol-2-yl)ethyl]-1H-indol-5-yl]methyl]-N-methylmethanesulphonamide (0.79 g) in ethanolic methylamine (33%; 18 ml) was kept at room temperature for 2½ h. The solvent was evaporated in vacuo and the residue re-evaporated with ethanol (2×30 ml). The residue was dissolved in a solution of maleic acid (0.65 g) in methanol (13 ml) and the maleate salt was precipitated by the addition of ethyl acetate (70 ml) and ether (380 ml). The salt was crystallised three times from a mixture of methanol and ethyl acetate to give the title compound (0.28 g) as pale cream crystals m.p. 155.5°–157°.

Analysis Found: C, 51.4; H, 5.9; N, 10.4; $C_{13}H_{19}N_3O_2S.C_4H_4O_4$ requires: C, 51.4; H, 5.8; N, 10.6%.

EXAMPLE 11

N-[[3-(2-Aminoethyl)-1H-indol-5-yl]methyl]-N-methyl-trifluoromethanesulphonamide, compound with creatinine, sulphuric acid and water (1:1:1:1)

(i)

N-[[3-[2-(1,3-Dihydro-1,3-dioxo-2H-isoindol-2-yl)ethyl]-1H-indol-5-yl]methyl]-N-methyltrifluoromethanesulphonamide In a similar manner to that described in Example 10(i), N-[[3-[2-(1,3-dihydro-1,3-dioxo-2H-isoindol-2-yl)ethyl]-1H-indol-5-yl]methyl]-trifluoromethanesulphonamide (1.04 g), sodium hydride (80%, 0.72 g) and methyl iodide (0.6 ml) in dimethylformamide (15 ml) gave the title compound (0.51 g) as a yellow solid m.p. 131°–3° after column chromatography on kieselgel 60 (80 g) eluted with ether/cyclohexane (4:1).

(ii)

N-[[3-(2-Aminoethyl)-1H-indol-5-yl]methyl]-N-methyl-trifluoromethanesulphonamide, compound with creatinine, sulphuric acid and water (1:1:1:1)

A solution of N-[[3-[2-(1,3-dihydro-1,3-dioxo-2H-isoindol-2-yl)ethyl]-1H-indol-5-yl]methyl]-N-methyltrifluoromethanesulphonamide (0.39 g) in ethanol (55 ml) was treated with hydrazine hydrate (0.70 ml) and heated at reflux for 1.5 h. After cooling, the mixture was evaporated to dryness, giving a white solid. This was partitioned between sodium carbonate solution (2N, 50 ml) and ethyl acetate (4×50 ml), and the combined organic extract was dried (magnesium sulphate) and evaporated to dryness, affording a yellow gum (0.33 g). This was dissolved in a hot mixture of ethanol (40 ml) and water (5 ml) and treated with an aqueous solution of creatinine and sulphuric acid (2M; 1:1; 0.44 ml). On cooling the title compound crystallised as a white solid (0.37 g) m.p. 237°–9° (d).

Analysis Found: C, 36.65; H, 4.8; N, 14.7. $C_{13}H_{16}F_3N_3O_2S.C_4H_7N_3O.H_2SO_4.H_2O$ requires: C, 36.2; H, 4.8; N, 14.9%.

EXAMPLE 12

N-[[3-(2-Aminoethyl)-1H-indol-5-yl]methyl]ethanesulphonamide, compound with creatinine, sulphuric acid and water (1:1:1:1)

(i)a

N-[[3-[2-(1,3-Dihydro-1,3-dioxo-2H-isoindol-2-yl)ethyl]-1H-indol-5-yl]methyl]ethanesulphonamide A mixture of 2-[2-[5-(aminomethyl)-1H-indol-3-yl]ethyl]-1H-isoindole-1,3(2H)-dione, hemisulphate, hydrate (1.11 g), ethanesulphonyl chloride (0.50 ml), sodium bicarbonate solution (8% aqueous; 40 ml) and ethyl acetate (40 ml) was stirred rapidly at room temperature for 1.5 h. The organic layer was then separated, and the aqueous phase further extracted with ethyl acetate (2×50 ml). The combined organic extract was washed with hydrochloric acid (2N; 50 ml), water (50 ml), dried (magnesium sulphate), and evaporated to dryness, giving a brown-black oil (1.30 g), which was purified by chromatography on a silica column (Kieselgel 60; 35 g) eluted with ether, affording the pure title compound as a yellow solid (0.28 g) m.p. 164°–7°.

The following compounds were similarly prepared from 2-[2-[5-(aminomethyl)-1H-indol-3-yl]ethyl]-1H-isoindole-1,3(2H)-dione, hemisulphate, hydrate and the appropriate sulphonyl chloride ($R_1SO_2Cl$) as detailed in Table 1.

TABLE 1

| Ex. No. | Wt. of starting material (g) | $R_1$ | Quantity $R_1SO_2Cl$ | Vol. of 8% NaHCO$_3$ (ml) | Vol. of EtOAc (ml) | Reaction time (h) | Wt. of product (g) | Mol. formula | m.p. °C. | Crystallization Solvent |
|---|---|---|---|---|---|---|---|---|---|---|
| 12 (i) b | 1.13 | —CHMe$_2$ | 1.4 g | 35 | 35 | 24 | 0.68 | $C_{22}H_{23}N_3O_4S$ · ½ $C_3H_8O$ | 171–3 | 2-propanol |
| 12 (i) c | 1.95 | ⬡ | 5.7 g | 150 | 150 | 42 | 0.81 | $C_{25}H_{27}N_3O_4S$ | 191–3 | ether[1] |
| 12 (i) d | 5.0 | Me | 1.4 ml | 150 | 150 | 0.5 | 4.23 | $C_{20}H_{19}N_3O_4S$ | 158–9 | Ethyl acetate |

[1]Purified by column chromatography on kieselgel 60 (100 g) eluted with ether.

(ii)a

N-[[3-(2-Aminoethyl)-1H-indol-5-yl]methyl]ethanesulphonamide, compound with creatinine, sulphuric acid and water (1:1:1:1)

A solution of N-[[3-[2-(1,3-dihydro-1,3-dioxo-2H-isoindol-2-yl)ethyl]-1H-indol-5-yl]methyl]ethanesulphonamide (0.70 g) in ethanol (100 ml) was treated with hydrazine hydrate (1.4 ml) and heated at reflux for 1 h. After cooling, the resulting solution was evaporated to dryness, and the resulting white solid was partitioned between sodium carbonate solution (2N; 80 ml) and ethyl acetate (3×80 ml). The organic extract was dried (magnesium sulphate) and evaporated to dryness, giving a yellow oil (0.49 g). This was dissolved in a hot mixture of ethanol (56 ml) and water (7 ml), and treated with an aqueous solution of creatinine and sulphuric acid (2M; 1:1; 0.85 ml). On cooling the title compound crystallised as a white solid (0.66 g) m.p. 206°–8° (d).

Analysis Found: C, 40.1; H, 5.9; N, 16.4; $C_{13}H_{19}N_3O_2S.C_4H_7N_3O.H_2SO_4.H_2O$ requires: C, 40.0; H, 5.9; N, 16.5%.

The following compounds were similarly prepared by deprotection of the appropriate starting material, as detailed in Table II.

The starting material prepared as in Example 12(i)d was deprotected using the process described in Example I(ii) to give N-[[3-(2-Aminoethyl)-1H-indol-5-yl]methyl]methanesulphonamide, compound with creatinine, sulphuric acid and water (1:1:1:1), m.p. 215°–8°.

Analysis Found: C, 38.5; H, 5.4; N, 16.8; $C_{12}H_{17}N_3O_2S.C_4H_7N_3O.H_2SO_4.H_2O$ requires: C, 38.7; H, 5.7; N, 16.95%.

TABLE II

| Ex. No. of product | Ex. No. of starting material $R_1$ | | Wt. of s.m. (g) | Vol. EtOH (ml) | Vol. $N_2H_4.H_2O$ (ml) | Wt. of product (g) | Molecular Formula | m.p. | Analysis Found | | | Required | | |
|---|---|---|---|---|---|---|---|---|---|---|---|---|---|---|
| | | | | | | | | | C % | H % | N % | C % | H % | N % |
| 12(ii)b | 12(i)b | —CHMe$_2$ | 0.46 | 90 | 0.9 | 0.35 | $C_{14}H_{21}N_3O_2S$.<br>$C_4H_7N_3O$.<br>$H_2SO_4.H_2O$ | 215–7° (d) | 41.1 | 5.9 | 15.7 | 41.2 | 6.15 | 16.0 |
| 12(ii)c | 12(i)c | 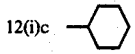 | 0.70 | 90 | 0.95 | 0.58 | $C_{17}H_{25}N_3O_2S$.<br>$C_4H_7N_3O$.<br>$H_2SO_4.H_2O$ | 221–4° (d) | 45.0 | 6.3 | 14.6 | 44.7 | 6.4 | 14.9 |

EXAMPLE 13

N-Methyl-N-[[3-[2-[(1-methyl-3-phenylpropyl)amino]ethyl]-1H-indol-5-yl]methyl]methanesulphonamide, compound with creatinine, sulphuric acid and water (1:1:1:1)

A solution of N-[[3-(2-aminoethyl)-1H-indol-5-yl]methyl]-N-methylmethanesulphonamide (0.4 g) and benzyl acetone (2 ml) in ethanol (70 ml) was hydrogenated at room temperature and pressure over palladium oxide on carbon (10%; 50% aq paste; 0.1 g; pre-reduced) until hydrogen uptake ceased.

The catalyst was filtered off and the filtrate evaporated to give a yellow oil which was dissolved in ethyl acetate (10 ml) and added dropwise to vigorously stirred petroleum ether (b.p. 60°–80°, 80 ml). The solvent was decanted off and the precipitated oil washed with petroleum ether (100 ml).

The washed oil (0.27 g) was dissolved in a hot mixture of ethanol (32 ml) and water (4 ml) and an aqueous solution of creatinine and sulphuric acid (2M; 1:1; 0.3 ml) was added. On cooling and scratching the title compound crystallised as a white solid (0.23 g) m.p. 142°–150.

Analysis Found: C, 50.0; H, 6.4; N, 12.8; $C_{23}H_{31}N_3O_2S.C_4H_7N_3O.H_2SO_4.H_2O$ requires: C, 50.4; H, 6.7; N, 13.05%.

EXAMPLE 14

N-[[3-[2-[(1-Methylethyl)amino]ethyl]-1H-indol-5-yl]methyl]methanesulphonamide, maleate A solution of N-[[3-(2-aminoethyl)-1H-indol-5-yl]methyl]methanesulphonamide (0.4 g) and acetone (2 ml) in ethanol (70 ml) was hydrogenated at room temperature and pressure over 10% palladium oxide on carbon (50% aqueous paste; 0.3 g; pre-reduced) until hydrogen uptake ceased. The catalyst was filtered off and the filtrate was evaporated to give a pale yellow oil (0.39 g).

A sample (0.30 g) was dissolved in hot methanol (ca 1 ml) and a solution of maleic acid (0.13 g) in hot methanol (½ ml) was added. On addition of dry ether (5 ml) and cooling the required maleate salt crystallised as a beige solid (0.28 g) m.p. 162.5°–163.5°.

Analysis Found: C, 53.6; H, 6.4; N, 9.7; $C_{15}H_{23}N_3O_2S.C_4H_4O_4$ requires: C, 53.6; H, 6.4; N, 9.9%.

EXAMPLE 15

N-[[3-[2-(Pyrrolidin-1-yl)ethyl]-1H-indol-5-yl]methyl]methanesulphonamide, oxalate (i)

5-[[(Methylsulphonyl)amino]methyl]-α-oxo-1H-indole-3-acetyl chloride

A solution of N-[(1H-indol-5-yl)methyl]methanesulphonamide (2.5 g) in dry tetrahydrofuran (40 ml) was added dropwise to dry ether (300 ml) and the solution was cooled in ice. Oxalyl chloride (2.3 ml) was added and the resulting yellow suspension stirred with ice cooling for 2¼ h. Further oxalyl chloride (1.0 ml) was added after 1½ h. The green solid was filtered off, washed with dry ether (50 ml) and dried in vacuo to give the title chloride (2.60 g) m.p. 135° (foams).

(ii)

1-[[5-[[(Methylsulphonyl)amino]methyl]-1H-indol-3-yl]oxoacetyl]pyrrolidine

Pyrrolidine (2.0 ml) was added to an ice-cooled, stirred solution of 5-[[(methylsulphonyl)amino]methyl]-α-oxo-1H-indole-3-acetyl chloride (2.5 g) in dry tetrahydrofuran (250 ml). The resulting milky suspension was stirred for 1 h, then warmed to room temperature for ½ h. The solution was decanted from the red oil onto 2N hydrochloric acid (150 ml) and ethyl acetate (100 ml). The layers were separated and the aqueous layer was extracted with ethyl acetate (3×50 ml). The organic extracts were dried ($Na_2SO_4$) and evaporated to give a pale pink solid which slowly darkened. Crystallisation twice from methanol gave the title compound as pale pink needles (0.24 g) m.p. 235°–6°.

(iii)

N-[[3-[2-(Pyrrolidin-1-yl)ethyl]-1H-indol-5-yl]methyl]methanesulphonamide, oxalate.

1-[[5-[[(Methylsulphonyl)amino]methyl]-1H-indol-3-yl]oxoacetyl]pyrrolidine (0.9 g) was added portionwise over ¼ h to a stirred suspension of lithium aluminium hydride (0.9 g) in dry tetrahydrofuran (60 ml) under nitrogen. The mixture was heated at reflux for 3 h and then allowed to cool. Aqueous tetrahydrofuran (15% $H_2O$; 20 ml) was added dropwise followed by water (40 ml). The grey mixture was saturated with solid sodium chloride and ethyl acetate (40 ml) was added. The mixture was filtered and the two phase filtrate separated. The aqueous phase was extracted with ethyl acetate (3×50 ml) and the combined extracts were dried ($Na_2SO_4$) and evaporated to give a white foam (0.84 g).

A portion of the foam (0.70 g) was dissolved in hot methanol (ca 8 ml) and a solution of oxalic acid (0.18 g) in hot methanol (ca 1 ml) was added. The resulting solution was quickly filtered hot, and then allowed to cool. The solid which crystallised was filtered off and dried to give the title amine oxalate as beige crystals (0.57 g) m.p. 201°–202° (dec).

Analysis Found: C, 52.3; H, 6.2; N, 10.25; $C_{16}H_{23}N_3O_2S.C_2H_2O_4$ requires: C, 52.4; H, 6.1; N, 10.2%.

EXAMPLE 16

N-[[3-(2-Aminopropyl)-1H-indol-5-yl]methyl]methanesulphonamide, maleate (i) N-[(3-Formyl-1H-indol-5-yl)methyl]methanesulphonamide Phosphorus oxychloride (12.0 ml) was added dropwise with ice cooling and stirring to dry dimethylformamide (100 ml). The solution was stirred for ¾ h and then a solution of N-[(1H-indol-5-yl)methyl]methanesulphonamide (5.0 g) was added over ½ h. The solution was stirred at 0° for ½ h, allowed to warm to room temperature, and stirred for 1¼ h. The yellow suspension was poured onto 25% aqueous potassium carbonate solution (400 ml) and the resulting solution was stirred for 1¾ h. The solid was filtered off and the filtrate left to stand for 24 h before extraction with ethyl acetate (6×200 ml). The combined extracts were washed with 20% brine (3×200 ml), dried ($Na_2SO_4$) and evaporated to dryness (1.01 g).

On leaving the sodium chloride washings to stand for 24 h, further material crystallised (2.30 g).

The two crops of solid were combined and recrystallised from a mixture of methanol and ethyl acetate to give the title sulphonamide as orange crystals (2.52 g) m.p. 181°-182°.

(ii) N-[[3-(2-Nitro-1-propenyl)-1H-indol-5-yl]methyl]methanesulphonamide

Ammonium acetate (0.8 g) was added in four equal portions at ½ hourly intervals to a solution of N-[(3-formyl-1H-indol-5-yl)methyl]methanesulphonamide (1.0 g) in nitroethane (50 ml) on a steam bath. After 2¼ h the resulting orange solution was poured onto water (100 ml). The aqueous layer was extracted with ethyl acetate (3×50 ml) and the combined organic extracts dried ($Na_2SO_4$) and evaporated to dryness. The residual yellow/brown solid (1.25 g) was dissolved in hot methanol (ca 50 ml) and the turbid solution was filtered. The filtrate was reduced in volume (to ca 10 ml) and allowed to cool to give the title sulphonamide as mustard crystals (0.86 g) m.p. 201°-202.5°.

(iii) N-[[3-(2-Aminopropyl)-1H-indol-5-yl]methyl]methanesulphonamide, maleate

A solution of N-[[3-(2-nitro-1-propenyl)-1H-indol-5-yl]methyl]methanesulphonamide (0.6 g) in dry tetrahydrofuran (30 ml) was added dropwise over 15 min, under nitrogen to a stirred suspension of lithium aluminium hydride (0.6 g) in dry tetrahydrofuran (30 ml). The mixture was heated to reflux with stirring for 5 h and then cooled in ice. Aqueous tetrahydrofuran (15% $H_2O$; 20 ml) was added dropwise followed by water (40 ml) and ethyl acetate (20 ml). The mixture was saturated with solid sodium chloride and filtered. The two phase filtrate was separated and the aqueous phase was extracted with ethyl acetate (2×50 ml). The combined extracts were dried ($Na_2SO_4$) and evaporated to give a colourless gum (0.62 g).

A portion of this gum (0.5 g) was dissolved in hot methanol (ca 3 ml) and a solution of maleic acid (0.21 g) in hot methanol (ca 1 ml) was added. On diluting with dry ether (ca 15 ml) and cooling a brown oil precipitated, which was triturated with dry ether (3×20 ml). Crystallisation of the resulting brown solid (0.45 g) from methanol (ca 4 ml) and ether (ca 14 ml) over 3 days gave the title maleate as a brown solid (0.27 g) m.p. 140°-142°.

Analysis Found: C, 51.5; H, 5.8; N, 10.6; $C_{13}H_{19}N_3O_2S.C_4H_4O_4$ requires: C, 51.4; H, 5.8; N, 10.5%.

EXAMPLE 17

N-[[3-(2-Amino-1-methylethyl)-1H-indol-5-yl]methyl]methanesulphonamide, compound with hydrochloric acid and diethyl ether (10:10:1)

(i) 5-Bromo-3-(1-methyl-2-nitroethyl)-1H-indole

Methyl iodide (35.5 g) was added to a stirred suspension of magnesium (4.8 g) in dry ether (100 ml) over a period of 10 min. To the grey solution was added a solution of 5-bromo-3-(2-nitroethenyl)-1H-indole (13.4 g) in dry tetrahydrofuran (250 ml) over a period of 1½ h. The resulting mass was stirred vigorously for 12 h, followed by the careful addition of saturated ammonium chloride (250 ml). After separation of the organic phase, the aqueous phase was extracted with ether (500 ml). The combined organic extracts were successively washed with 5% sodium sulphite solution (500 ml) and water (500 ml). Evaporation of the dried ($MgSO_4$) ethereal phase gave a brown oil which was chromatographed on Kieselgel 60 using diethyl ether as eluant to give the title compound as a yellow gum (7.03 g) T.L.C. silica/diethyl ether Rf 0.5.

(ii) 5-Bromo-β-methyl-1H-indole-3-ethanamine

A solution of 5-bromo-3-(1-methyl-2-nitroethyl)-1H-indole (7.0 g) in dry tetrahydrofuran (100 ml) was added to a stirred suspension of lithium aluminium hydride (1.88 g) in dry tetrahydrofuran (50 ml) under a stream of nitrogen. The mixture was heated under reflux for 8 h, cooled in an ice bath and 2N sodium hydroxide solution (6 ml) was added cautiously. Filtration of the suspension through Hyflo and evaporation of the filtrate gave an amber oil which was chromatographed on kieselgel 60 eluted with methanol to give the title amine as a yellow gum (3.5 g) T.L.C. silica, methanol/ammonia (79:13) Rf 0.27.

(iii) 2-[2-[(5-Bromo-1H-indol-3-yl)-2-methyl]ethyl]-1H-isoindole-1,3(2H)-dione

A mixture of 5-bromo-β-methyl-1H-indole-3-ethanamine (3.5 g) and phthalic anhydride (2.24 g) was heated under reflux in acetic acid (50 ml) containing sodium acetate (1.2 g) for 2 h.

Evaporation of the solvent gave a red gum which was dissolved in ethyl acetate (200 ml). The solution was washed successively with 2N hydrochloric acid (100 ml), 8% sodium bicarbonate (100 ml) and water (100 ml). The dried ($MgSO_4$) solution was evaporated and the solid crystallised from aqueous 2-propanol to give the title compound as a fluffy pink solid (3.9 g) m.p. 153°-5°.

(iv) 3-[2-(1,3-Dihydro-1,3-dioxo-2H-isoindol-2-yl)-1-methylethyl]-1H-indole-5-carbonitrile A mixture of 2-[2-[(5-bromo-1H-indol-3-yl)-2-methyl]ethyl]-1H-isoindole-1,3(2H)-dione (3.9 g) and cuprous cyanide (1.37 g) was heated under reflux in N-methyl-2-pyrrolidone (50 ml) under nitrogen. After 2 h the cooled mixture was poured into iced water (200 ml) containing 880 ammonia (20 ml). The resulting suspension was shaken with ethyl acetate (200 ml) and subsequently filtered through Hyflo. The aqueous phase was extracted with ethyl acetate (2×100 ml) and the combined organic extracts were dried (MgSO$_4$). Evaporation of the solvent gave a brown gum which was chromatographed on kieselgel 60 eluted with diethyl ether to give the title compound as an off-white solid (2.05 g) m.p. 218°–220° after crystallisation from ethanol.

(v)

3-[2-(1,3-Dihydro-1,3-dioxo-2H-isoindol-2-yl)-1-methylethyl]-1H-indole-5-methanamine A suspension of 3-[2-[1,3-dihydro-1,3-dioxo-2H-isoindol-2-yl]1-methylethyl]-1H-indole-5-carbonitrile (1.4 g) and pre-reduced 10% palladium on charcoal (1.4 g) in methanol (100 ml) containing concentrated sulphuric acid (0.5 ml) was hydrogenated at room temperature and pressure until hydrogen uptake ceased. The catalyst was filtered off and the filtrate was evaporated to dryness to give a red oil (3.3 g) which was used without further purification.

(vi)

N-[[3-[2-[1,3-Dihydro-1,3-dioxo-2H-isoindol-2-yl]-1-methylethyl]-1H-indol-5-yl]methyl]methanesulphonamide A stirred solution of 3-[2-(1,3-dihydro-1,3-dioxo-2H-isoindol-2-yl)-1-methylethyl]-1H-indole-5-methanamine (3.29 g) in dry pyridine (50 ml) cooled in an ice bath was treated with methanesulphonyl chloride (1.64 ml). After 18 h at room temperature the solvent was removed under reduced pressure and the resulting viscous orange oil poured into a mixture of ice and concentrated hydrochloric acid (200 ml) to give a pink solid which was purified by chromatography on kieselgel 60 (200 g) eluted with ethyl acetate/cyclohexanane (1:1) to give the title compound as a yellow foam (0.28 g). This material was used without further purification.

(vii)

N-[[3-[2-Amino-1-methylethyl]-1H-indol-5-yl]methyl]-methanesulphonamide, compound with hydrochloric acid and diethyl ether (10:10:1)

A solution of N-[[3-[2-(1,3-dihydro-1,3-dioxo-2H-isoindol-2-yl)-1-methylethyl]-1H-indol-5-yl]methyl]methanesulphonamide (0.21 g) and hydrazine hydrate (0.15 ml) in ethanol (20 ml) was heated under reflux for 2.5 h, then the solvent was removed under reduced pressure. The resulting white solid was partitioned between ethyl acetate (20 ml) and aqueous potassium carbonate solution (20 ml). The layers were separated, and the aqueous layer was extracted with ethyl acetate (3×25 ml), dried over magnesium sulphate and evaporated. The resulting gummy foam was treated in ethanol with ethereal hydrogen chloride solution, adding ether to precipitate the salt. The solid was collected, washed thoroughly with dry ether and dried in vacuo to give the title compound as a yellow solid (0.12 g) m.p. 228°–231° (foaming).

Analysis Found: C, 49.2; H, 6.5; N, 12.6%; $C_{13}H_{19}N_3O_2S.HCl.0.1C_4H_{10}O$ requires: C, 49.4; H, 6.5; N, 12.9%.

EXAMPLE 18

N-[[3-[2-[(2-Propenyl)amino]ethyl]-1H-indol-5-yl]methyl]methanesulphonamide, maleate (i)

5-[[(Methylsulphonyl)amino]methyl]-α-oxo-N-(2-propenyl)-1H-indole-3-acetamide, quarter hydrate Allylamine (5.5 ml) was added dropwise to an ice-cooled, stirred solution of 5-[[(methylsulphonyl)amino]methyl]-α-oxo-1H-indole-3-acetyl chloride (11.4 g) in dry tetrahydrofuran (250 ml). The yellow solution was stirred at 0° for 1 h and then at room temperature for 2.25 h (further allylamine (2 ml) was added after 0.75 h). Water (20 ml) was added and stirring was continued for 10 min. The mixture was then poured onto 2N hydrochloric acid (500 ml) and ethyl acetate (200 ml). The solid which precipitated was filtered off and dried (Crop I). The two layers in the filtrate were separated and the aqueous layer was extracted with ethyl acetate (2×500 ml). The combined extracts were dried (Na$_2$SO$_4$) and evaporated to give a dark green solid (Crop II).

The two crops of solid were combined and treated with charcoal in a refluxing mixture of chloroform (300 ml) and methanol (100 ml) for 1.5 h. The mixture was filtered hot and the filtrate was reduced in volume. The solid which crystallised on cooling was filtered off, washed with ice-cold methanol (30 ml) and ether (3×30 ml) and dried to give the title acetamide as fawn crystals (4.5 g), m.p. 234°–235°.

(ii)

N-[[3-[2-[(2-Propenyl)amino]ethyl]-1H-indol-5-yl]methyl]methanesulphonamide, maleate A suspension of 5-[[(methylsulphonyl)amino]methyl]-α-oxo-N-(2-propenyl)-1H-indole-3-acetamide, quarter hydrate (1.0 g) in dry tetrahydrofuran (50 ml) was added dropwise to an ice-cooled, stirred suspension of lithium aluminium hydride (1.2 g) in dry tetrahydrofuran (50 ml), under nitrogen, over 0.25 h. The resulting brick red suspension was stirred at 0° for 10 min., heated to reflux and stirred for 27.5 h. The green suspension was allowed to cool and then aqueous tetrahydrofuran (15% H$_2$O, 25 ml) was added dropwise, followed by water (50 ml) and ethyl acetate (70 ml). The mixture was saturated with solid sodium chloride and filtered. The two phases in the filtrate were separated and the aqueous phase was extracted with ethyl acetate (2×50 ml). The combined organic extracts were dried (Na$_2$SO$_4$) and evaporated to give a dark orange oil (0.93 g) which was dissolved in hot methanol (ca. 10 ml) and a solution of maleic acid (0.34 g) in hot methanol (ca. 1 ml) was added. On dilution with ethyl acetate (ca. 75 ml), cooling and scratching a brown solid crystallised.

Recrystallisation from a mixture of methanol (4 ml) and ethyl acetate (15 ml) gave the title compound as a light brown solid (0.32 g) m.p. 148°–150°.

Analysis Found: C, 53.9; H, 5.8; N, 9.65; $C_{15}H_{21}N_3O_2.C_4H_4O_4$ requires: C, 53.9; H, 5.95; N, 9.9%.

EXAMPLE 19

N-[[3-(2-Aminoethyl)-1H-indol-5-yl]methyl]methanesulphonamide (i) N-[(4-Nitrophenyl)methyl]methanesulphonamide A mixture of N-(methylsulphonyl)acetamide potassium salt (23 g) and 4-nitrobenzyl bromide (24 g) in dry DMF (160 ml) was stirred in an oil bath at 130° for 2 h. After standing overnight at room temperature, a solution of sodium hydroxide (8 g) in water (50 ml) was added and the mixture stirred under nitrogen for 0.75 h. The mixture was diluted with water (900 ml) and the product extracted into ethyl acetate (2×400 ml). The combined extract was washed with brine (3×200 ml), dried (Na$_2$SO$_4$) and evaporated in vacuo to leave an orange solid (22 g).

Crystallisation from ethyl acetate gave the title compound (7 g) as yellow crystals m.p. 136°–9°.

(ii) N-[(4-Aminophenyl)methyl]methanesulphonamide

A solution of N-[(4-nitrophenyl)methyl]methanesulphonamide (2.5 g) in a mixture of ethanol (90 ml) and ethyl acetate (90 ml) was hydrogenated at room temperature and pressure over palladium oxide on charcoal (10%; 50% paste with water, 1 g) until uptake of hydrogen ceased (15 min., 820 ml).

The catalyst was filtered off and the filtrate evaporated in vacuo to leave the title compound (2.15 g) as a very pale cream solid, m.p. 144°–9° (some softening at 135°).

(iii) N-[(4-Hydrazinophenyl)methyl]methanesulphonamide, hydrochloride

A solution of sodium nitrite (0.3 g) in water (3 ml) was added, over 15 min. to a stirred suspension of N-[(4-aminophenyl)methyl]methanesulphonamide (0.7 g) in concentrated hydrochloric acid (3 ml) and water (4 ml) keeping the temperature below 0°. After 1 h, the resulting suspension was added, over 1 min. to a stirred, ice-cooled solution of sodium acetate (3.2 g) and sodium sulphite (1.8 g) in water (20 ml) containing ice (5 g). The orange mixture was stirred for a further 30 min. then at room temperature for 1.5 h, and then warmed on the steam bath for 20 min. The mixture was cooled, concentrated hydrochloric acid (15 ml) added and the mixture warmed on the steam bath for 0.5 h. The solvent was evaporated in vacuo and the residue re-evaporated with absolute ethanol (2×50 ml). The residue was extracted with absolute ethanol (50 ml). The extract was evaporated in vacuo and the residue re-evaporated with ethanol (20 ml) to leave a brown oil, which partially crystallised after standing overnight. Ethanol (1 ml) was added and the title compound filtered off as light tan crystals (0.1 g) m.p. 165°–70° (dec.)

(iv) N-[[3-(2-Aminoethyl)-1H-indol-5-yl]methyl]methanesulphonamide

A mixture of N-[(4-hydrazinophenyl)methyl]methanesulphonamide hydrochloride (0.02 g), 4-chlorobutanal diethylacetal (0.02 ml), acetic acid (1 drop), methanol (0.5 ml) and water (2 drops) was warmed briefly on the steam bath then allowed to stand for 15 min. The mixture was then refluxed for 3 h.

TLC silica, ethyl acetate, 2-propanol, water, 0.88 ammonia (25:15:8:2) showed the title compound as the major basic product R$_f$ 0.35, identical to an authentic sample (see Example 1).

EXAMPLE 20

N-[[3-[2-(Methylamino)ethyl]-1H-indol-5-yl]methyl]-methanesulphonamide (i) Ethyl 5-[[(methylsulphonyl)amino]methyl]-α-oxo-1H-indole-3-acetate 5-[[(Methylsulphonyl)amino]methyl]-α-oxo-1H-indole-3-acetyl chloride (1.14 g) was suspended in absolute ethanol (60 ml) and triethylamine (0.5 ml) was added and the mixture heated under reflux for 2 h. The solid quickly dissolved to give a dark yellow solution. A pale buff solid separated on cooling. The mixture was concentrated to low volume and the solid was collected, washed with water (30 ml) and ethanol (20 ml) to give the title compound, (0.97 g) m.p. 218°–220°.

Recrystallisation of a small sample from ethanol gave material, m.p. 216°–219°.

(ii) N-[[3-(2-Hydroxyethyl)-1H-indol-5-yl]methyl]methanesulphonamide

Ethyl 5-[[(methylsulphonyl)amino]methyl]-α-oxo-1H-indole-3-acetate (0.50 g) was added portionwise under nitrogen to a stirred suspension of lithium aluminium hydride (0.59 g) in dry THF (30 ml). The mixture was heated under reflux for 6 h, then cooled in an ice bath and treated dropwise with aqueous THF (15%, 20 ml) and then with water (20 ml) and extracted with ethyl acetate (6×25 ml). The extract was washed with brine (3×25 ml) and dried (Na$_2$SO$_4$). Removal of the solvent gave a dark brown oil which was purified by chromtography on a silica column (Merck Kieselgel 60; 10 g) eluted with cyclohexane then ethyl acetate to give the title compound as a gum (0.3 g) which failed to crystallise TLC silica, ethyl acetate. R$_f$ 0.54 detected by UV and Ce(SO$_4$)$_2$ τ (DMSO) 6.32 (2H, q), 7.15 (2H, t) CH$_2$CH$_2$OH.

(iii) N-[[3-(2-Bromoethyl)-1H-indol-5-yl]methyl]methanesulphonamide

Phosphorus tribromide (0.03 ml) was added dropwise to a solution of N-[[3-(2-hydroxyethyl)-1H-indol-5-yl]methyl]methanesulphonamide (0.18 g) in dry THF (20 ml) stirred in an ice bath. There was an immediate reddish colour produced. The solution was stirred for 2 h and then at room temperature for a further 3.5 h, then again chilled in ice, diluted with water (40 ml) and extracted with ether (2×50 ml, 3×25 ml) combined extracts were washed with brine (3×20 ml) and dried (Na$_2$SO$_4$). Removal of the solvent by rotary evaporation at 35°–40° afforded the title compound as a viscous pink oil (0.22 g).

TLC silica, ethyl acetate showed two indolic spots R$_f$ 0.86 and 0.29 (u.v. and Ce(SO$_4$)$_2$).

This material was used without further purification.

(iv) N-[[3-[2-(Methylamino)ethyl]-1H-indol-5-yl]methyl]-methanesulphonamide

Crude N-[[3-(2-bromoethyl)-1H-indol-5-yl]methyl]-methanesulphonamide (0.2 g) was taken up in 33% ethanolic methylamine (20 ml) to give a yellow solution which was allowed to stand at room temperature for 17 h. The yellow colour disappeared within about 1 h.

TLC silica, ethyl acetate, 2-propanol, water, 0.88 ammonia (25:15:8:2) showed one basic product spot. $R_f$ 0.4 identical to an authentic sample (see Example 2).

EXAMPLE 21

N-[1-[3-(2-Aminoethyl)-1H-indol-5-yl]ethyl]methanesulphonamide, compound with creatinine, sulphuric acid and water (1:1:1:1)

(i)
2-[2-(5-Acetyl-1H-indol-3-yl)ethyl]-1H-isoindole-1,3(2H)-dione

A suspension of 5-acetyl-1H-indole-3-ethanamine (1.0 g), phthalic anhydride (0.83 g) and sodium acetate (1.0 g) in acetic acid (15 ml) was heated at reflux for 3 h. On cooling the title compound was deposited as an off-white crystalline solid (1.5 g) m.p. 234°–5°.

(ii)
2-[5-[1-(Hydroxyimino)ethyl]-1H-indol-3-yl]-1H-isoindole-1,3(2H)-dione

A suspension of 2-[2-(5-acetyl-1H-indol-3-yl)ethyl]-1H-isoindole-1,3-(2H)-dione (1.0 g) in ethanol (20 ml) was treated with a solution of hydroxylamine acetate [generated from a solution of hydroxylamine hydrochloride (0.5 g) and sodium acetate (0.5 g) in water (5 ml) diluted with ethanol (75 ml) to deposit sodium chloride]. The reaction mixture was heated at reflux for 2.5 h. On cooling the title compound crystallised out as yellow solid (1.0 g) m.p. 220°–223°.

(iii)
N-[1-[3-[2-(1,3-Dihydro-1,3-dioxo-2H-isoindol-2-yl)ethyl]-1H-indol-5-yl]ethyl]methansulphonamide, hemihydrate A suspension of 2-[5-[1-(hydroxyimino)ethyl]-1H-indol-3-yl]-1H-isoindole-1,3(2H)-dione (0.88 g) in methanol (150 ml) and concentrated sulphuric acid (0.8 ml) was hydrogenated over pre-reduced palladium on charcoal (0.8 g) at room temperature and pressure until hydrogen uptake ceased (4 h, 120 ml). The catalyst was filtered off, washed with methanol and the filtrate evaporated to dryness, keeping the temperature below 40°. The resulting red/brown oil was dissolved in ethyl acetate (50 ml) and sodium bicarbonate (8%, 150 ml) and treated with methanesulphonyl chloride (0.23 ml) with vigorous stirring. After 2 h the organic layer was separated and the aqueous phase extracted with ethyl acetate (2×50 ml). The combined organic extract was washed with dilute hydrochloric acid (2N, 2×50 ml), water (50 ml), dried (Na$_2$SO$_4$) and evaporated to dryness to give a yellow oil. This was purified on a silica column (Kieselgel 60, 75 g) eluted with chloroform to give the title compound as a white solid (0.4 g), m.p. 203°–5° after crystallisation from ethyl acetate.

(iv)
N-[1-[3-(2-Aminoethyl)-1H-indol-5-yl]ethyl]methanesulphonamide, compound with creatinine, sulphuric acid and water (1:1:1:1)

A solution of N-[1-[3-[2-(1,3-dihydro-1,3-dioxo-2H-isoindol-2-yl)ethyl]-1H-indol-5-yl]ethyl]methanesulphonamide (0.35 g) in ethanol (50 ml) and hydrazine hydrate (0.25 ml) was heated at reflux for 2 h. The reaction mixture was evaporated to dryness and partitioned between ethyl acetate (100 ml) and sodium carbonate (2N, 100 ml). The aqueous phase was washed with ethyl acetate (4×50 ml) and the combined organic phase dried (Na$_2$SO$_4$) and evaporated to dryness to give a white solid. This was dissolved in a hot mixture of ethanol (25 ml) and water (2 ml) and treated with creatinine sulphate solution (2M, 1:1, 0.4 ml) to deposit the title compound as a white crystalline solid (0.35 g) on cooling, m.p. 195°–7°.

Analysis Found: C, 39.5; H, 5.7; N, 16.3; C$_{13}$H$_{19}$N$_3$O$_2$S.C$_4$H$_7$N$_3$O.H$_2$SO$_4$.H$_2$O requires: C, 40.0; H, 5.9; N, 16.5%.

EXAMPLE 22

N-[[3-[2-(Methylamino)ethyl]-1H-indol-5-yl]methyl]methanesulphonamide

(i)
N-[[3-[(Dimethylamino)methyl]-1H-indol-5-yl]methyl]methanesulphonamide, compound with ethyl acetate and water (10:2:2)

Aqueous formaldehyde (37%, 0.8 ml) was added dropwise to an ice cooled, stirred, solution of aqueous dimethylamine (40%, 1.35 ml) in glacial acetic acid (16 ml) and the resulting solution stirred at room temperature for 15 min. A suspension of N-[(1H-indol-5-yl)methyl]methanesulphonamide (2.7 g) in glacial acetic acid (16 ml) was added, and the resulting suspension stirred until a solution was obtained (10 min).

Water (20 ml) was added and the resulting solution basified (K$_2$CO$_3$) and extracted with ethyl acetate (2×50 ml). The combined extracts were extracted with hydrochloric acid (2N, 100 ml). The aqueous acid extract was basified (K$_2$CO$_3$) and extracted with ethyl acetate (2×100 ml). The combined organic extracts were dried (Na$_2$SO$_4$) and evaporated in vacuo to give the title compound as an off-white foam (0.95 g) which failed to crystallise from common organic solvents and failed to form a solid salt.

TLC Silica, Ethyl acetate/2-propanol/water/0.88 ammonia (25:15:8:2) Rf 0.5 detection UV and iodoplatinic acid.

(ii)
N-[[3-(Cyanomethyl)-1H-indol-5-yl]methyl]methanesulphonamide

Methyl iodide (0.15 ml) was added to a stirred solution of N-[[3-[(dimethylamino)methyl]-1H-indol-5-yl]methyl]methanesulphonamide (0.5 g) in dimethyl sulphoxide (20 ml) followed by potassium cyanide (0.3 g) and the resulting solution stirred for 2 h, before pouring it into water (80 ml) and extracting with ethyl acetate (2×30 ml). The combined organic extracts were washed with water (30 ml), hydrochloric acid (2N, 30 ml) dried (Na$_2$SO$_4$) and evaporated to dryness to give a fawn foam which was purified on a silica column (kieselgel 60, 10 g) eluted with ethyl acetate to give the title compound as a white solid (0.08 g) m.p. 106°–9° after crystallisation from ethyl acetate.

(iii)
N-[[3-[2-(Methylamino)ethyl]-1H-indol-5-yl]methyl]methanesulphonamide

A solution of N-[[3-(cyanomethyl)-1H-indol-5-yl]methyl]methanesulphonamide (0.04 g) in absolute ethanol (10 ml) containing methylamine in ethanol, (33%, 0.5 ml) was hydrogenated at room temperature and pressure over palladium on charcoal (10%, 50% aqueous paste, 0.05 g). After 60 h TLC Silica, ethyl acetate/2- propanol/water/0.88 ammonia (25:15:2) showed one major basic spot Rf 0.4, identical to authentic product (see Example 2)

PHARMACEUTICAL EXAMPLES

Tablets

These may be prepared by direct compression or wet granulation. The direct compression method is preferred but may not be suitable in all cases as is dependent upon the dose level and physical characteristics of the active ingredient.

| A. Direct Compression | mg/tablet |
|---|---|
| Active ingredient | 10.0 |
| Microcrystalline Cellulose B.P.C. | 89.5 |
| Magnesium Stearate | 0.5 |
| | 100.0 |

The active ingredient is sieved through a 250 μm sieve, blended with the excipients and compressed using 6.0 mm punches. Tablets of other strengths may be prepared by altering the compression weight and using punches to suit.

| B. Wet Granulation | mg/tablet |
|---|---|
| Active ingredient | 10.0 |
| Lactose B.P. | 74.5 |
| Starch B.P. | 10.0 |
| Pregelatinised Maize Starch B.P. | 5.0 |
| Magnesium Stearate B.P. | 0.5 |
| Compression Weight | 100.0 |

The active ingredient is sieved through a 250 μm sieve and blended with the lactose, starch and pregelatinised starch. The mixed powders are moistened with purified water, granules are made, dried, screened and blended with the Magnesium Stearate. The lubricated granules are compressed into tablets as described for the direct compression formulae.

The tablets may be film coated with suitable film forming materials, e.g. methyl cellulose or hydroxypropyl methyl cellulose using standard techniques. Alternatively the tablets may be sugar coated.

| Capsules | mg/capsule |
|---|---|
| Active ingredient | 10.0 |
| *Starch 1500 | 89.5 |
| Magnesium Stearate B.P. | 0.5 |
| Fill Weight | 100.0 |

*A form of directly compressible starch supplied by Coloron Ltd., Orpington, Kent.

The active ingredient is sieved through a 250 μm sieve and blended with the other materials. The mix is filled into No. 2 hard gelatin capsules using a suitable filling machine. Other doses may be prepared by altering the fill weight and if necessary changing the capsule size to suit.

| Syrup | mg/5 ml dose |
|---|---|
| Active ingredient | 10.0 |
| Sucrose B.P. | 2750.0 |
| Glycerine B.P. | 500.0 |
| Buffer | |
| Flavour | |
| Colour | as required |
| Preservative | |

| Syrup | mg/5 ml dose |
|---|---|
| Distilled Water | 5.00 ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| Suppositories | |
|---|---|
| Active ingredient | 10.0 mg |
| *Witepsol H15 to | 1.0 g |

*A proprietary grade of Adeps Solidus ph. Eur.

A suspension of the active ingredient in the matter Witepsol H15 is prepared and filled using a suitable machine into 1 g size suppository moulds.

INJECTION FOR INTRAVENOUS ADMINISTRATION

| | % w/v |
|---|---|
| Active ingredient | 0.20 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere to nitrogen.

INHALATION CARTRIDGES

| | mg/cartridge |
|---|---|
| Active ingredient micronised | 1.00 |
| Lactose B.P. | 39.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler (e.g. Glaxo Rotahaler).

METERED DOSE PRESSURISED AEROSOL

| | mg/metered dose | Per can | |
|---|---|---|---|
| Active ingredient micronised | 0.500 | 120 | mg |
| Oleic Acid B.P. | 0.050 | 12 | mg |
| Trichlorofluoromethane B.P. | 22.25 | 5.34 | g |
| Dichlorodifluoromethane B.P. | 60.90 | 14.62 | g |

The active ingredient is micronised in a fluid energy mill to a fine particle size range. The Oleic Acid is mixed with the Trichlorofluoromethane at a temperature of 10°–15° C. and the micronised drug is mixed into this solution with a high shear mixer. The suspension is metered into aluminium aerosol cans and suitable metering valves, delivering a metered dose of 85 mg of suspension are crimped onto the cans and the Dichlorodifluoromethane is pressure filled into the cans through valves.

We claim:

1. A compound of the formula I:

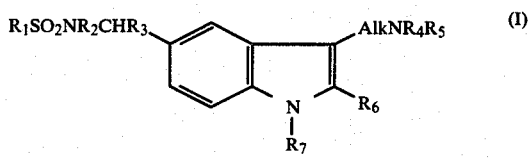 (I)

wherein $R_1$ represents a $C_{1-6}$ alkyl, $C_{5-7}$ cycloalkyl, aryl or ara $C_{1-4}$ alkyl group; $R_2$, $R_3$, $R_4$, $R_6$ and $R_7$, which may be the same or different, each represents a hydrogen atom or a $C_{1-3}$ alkyl group; $R_5$ represents a hydrogen atom or a $C_{1-6}$ alkyl, $C_{5-7}$ cycloalkyl, $C_{3-6}$ alkenyl or ara $C_{1-4}$ alkyl group; or $R_4$ and $R_5$ together form an aralkylidene group or $R_4$ and $R_5$ together with the nitrogen atom to which they are attached form a saturated monocyclic 5- to 7-membered ring; Alk represents an alkylene chain containing two or three carbon atoms which may be unsubstituted or substituted by not more than two $C_{1-3}$ alkyl groups; aryl, alone or as part of a group means phenyl which may be optionally substituted with one or more substitutes selected from the group consisting of $C_{1-3}$ alkyl, $C_{1-3}$ alkoxy and halogen atoms; and physiologically acceptable salts and solvates thereof.

2. A compound according to claim 1, wherein $R_1$ represents an alkyl group containing 1 to 3 carbon atoms.

3. A compound according to claim 1, wherein $R_2$ represents a hydrogen atom or a methyl group and $R_3$ represents a hydrogen atom.

4. A compound according to claim 1, wherein Alk represents an unsubstituted alkylene chain containing two carbon atoms.

5. A compound according to claim 1, wherein $R_4$ and $R_5$, which may be the same or different, each represents a hydrogen atom or a methyl or ethyl group and $R_6$ and $R_7$ each represents a hydrogen atom.

6. A compound according to claim 1 having the general formula (Ia):

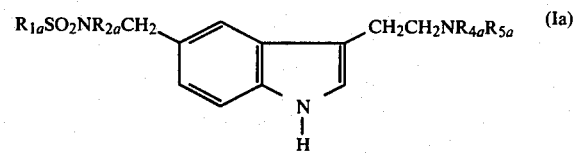

wherein
$R_{1a}$ represents an alkyl group containing 1 to 3 carbon atoms, or a trifluoromethyl group;
$R_{2a}$ represents a hydrogen atom or a methyl group;
$R_{4a}$ and $R_{5a}$, which may be the same or different, each represents a hydrogen atom or a methyl or ethyl group;
and physiologically acceptable salts and solvates thereof.

7. A compound according to claim 6 having the general formula (Ib):

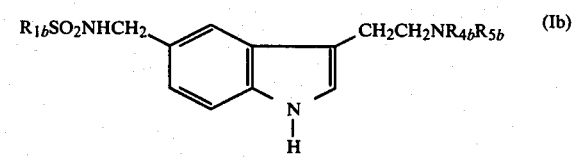

wherein
$R_{1b}$ represents an alkyl group containing 1 to 3 carbon atoms;
$R_{4b}$ and $R_{5b}$, which may be the same or different, each represents a hydrogen atom or a methyl or ethyl group, such that the total number of carbon atoms in $R_{4b}$ and $R_{5b}$ together does not exceed two;
and physiologically acceptable salts and solvates thereof.

8. A compound according to claim 1, wherein $R_1$ represents an alkyl group containing 1 to 3 carbon atoms, $R_2$ represents a hydrogen atom or a methyl group and $R_3$ represents a hydrogen atom; Alk represents an unsubstituted alkylene chain containing two carbon atoms; $R_4$ and $R_5$, which may be the same or different, each represents a hydrogen atom or a methyl or ethyl group and $R_6$ and $R_7$ each represent a hydrogen atom.

9. N-[[3-[2-(Methylamino)ethyl]-1H-indol-5-yl]methyl]methanesulphonamide and physiologically acceptable salts and solvates thereof.

10. N-[[3-[2-(Dimethylamino)ethyl]-1H-indol-5-yl]methyl]methanesulphonamide and physiologically acceptable salts and solvates thereof.

11. A compound according to claim 1 wherein the physiologically acceptable salt is a hydrochloride hydrobromide sulphate, fumarate or a maleate.

12. A pharmaceutical composition comprising at least one compound of formula (I) as defined in claim 1 or a physiologically acceptable salt or solvate thereof together with one or more physiologically acceptable carriers or excipients.

13. A method of treating a patient suffering from migraine which comprises administering to a patient suffering from migraine the composition as claimed in claim 12.

* * * * *